(12) United States Patent
Kiss

(10) Patent No.: US 7,312,198 B2
(45) Date of Patent: Dec. 25, 2007

(54) PROTEIN COMPOSITIONS FOR PROMOTING WOUND HEALING AND SKIN REGENERATION

(75) Inventor: Zoltan Kiss, Austin, MN (US)

(73) Assignee: Essential Skincare, LLC, Austin, MN (US)

( * ) Notice: Subject to any disclaimer, the term of this patent is extended or adjusted under 35 U.S.C. 154(b) by 0 days.

(21) Appl. No.: 11/430,574

(22) Filed: May 9, 2006

(65) Prior Publication Data

US 2007/0014777 A1 Jan. 18, 2007

Related U.S. Application Data

(60) Provisional application No. 60/698,321, filed on Jul. 12, 2005.

(51) Int. Cl.
*A61K 38/00* (2006.01)
*C07K 14/00* (2006.01)
*C12N 9/00* (2006.01)

(52) U.S. Cl. .................. 514/12; 530/350; 530/395; 435/183; 424/94.6

(58) Field of Classification Search ............... 435/183; 424/94.6; 514/12; 530/350, 395
See application file for complete search history.

(56) References Cited

U.S. PATENT DOCUMENTS

| 4,347,841 A | 9/1982 | Benyó |
| 5,461,030 A | 10/1995 | Lindenbaum |
| 5,556,645 A | 9/1996 | Bockman et al. |
| 5,591,709 A | 1/1997 | Lindenbaum |
| 7,011,965 B2 | 3/2006 | Kiss |

FOREIGN PATENT DOCUMENTS

RU 1814764 A3 * 3/1995

OTHER PUBLICATIONS

Martin, P. (1997) *Wound healing—Aiming for perfect skin regeneration.* Science 276, 75-81.
Werner et al., (2003) *Regulation of wound healing by growth factors and cytokines.* Physiol. Rev. 10, 835-870.
Yamasaki et al., (2003) *Keratinocyte growth inhibition by high-dose epidermal growth factor is mediated by transforming growth factor β autoinduction: A negative feedback mechanism for keratinocyte growth.* J. Invest. Dermatol. 120, 1030-1037.
Janciauskiene, (2001) *Conformational properties of serine proteinase inhibitors (serpins) confer multiple pathophysiological roles.* Biochim. Biophys. Acta 1535, 221-235.
Perraud et al., (1988) *Proliferation of rat astrocytes, but not of oligodendrocytes, is stimulated in vitro by protease inhibitors.* Int. J. Devl. Neuroscience 6, 261-266.
She et al., (2000) $\alpha_1$-*Antitrypsin can increase insulin-induced mitogenesis in various fibroblast and epithelial cell lines.* FEBS Lett. 473, 33-36.
Dabbagh et al., (2001) *Alpha-1-antitrypsin stimulates fibroblast proliferation and procollagen production and activates classical MAP kinase signaling pathways.* J. Cell. Physiol. 186, 73-81.
Bergman et al., (1993) *Synthesis of $\alpha_1$-antichymotrypsin and $\alpha_1$-antitrypsin by human trophoblast.* Pediatric Res. 34, 312-317.
Niemann et al., (1997), *Inhibition of human serine proteases by SPAAT, the C-terminal 44-residue peptide from $\alpha_1$-antitrypsin.* Biochim. Biophys. Acta 1340, 123-130.
Leicht et al., (1982) *Sequence homology and structural comparison between the chromosomal human $\alpha_1$-antitrypsin and chicken ovalbumin genes.* Nature 297, 655-659.
Long et al., (1984) *Complete Sequence of the cDNA from human $\alpha_1$-antitrypsin and the gene for the S variant.* Biochemistry 23, 4828-4837.
Kwon et al., (1994) *Single amino acid substitutions of $\alpha_1$-antitrypsin that confer enhancement in thermal stability.* J. Biol. Chem. 269, 9627-9631.
Kataoka et al., (1999) *Enhanced tumor growth and invasiveness in vivo by a carboxyl-terminal fragment of $\alpha_1$-proteinase inhibitor generated by matrix metalloproteinases: A possible modulatory role in natural killer cytotoxicity.* American J. Pathol. 154, 457-468.
J.L. Millan et al., (1995) *Biology of human alkaline phosphatases with special reference to cancer.* Critical Reviews in Clinical Sciences 32, 1-39.
She et al., (2000) *Growth factor-like effects of placental alkaline phosphatase in human fetus and mouse embryo fibroblasts.* FEBS Letters, 468, 163-167.
She et al., (2000) *Placental alkaline phosphatase, insulin, and adenine nucleotides or adenosine synergistically promote long-term survival of serum-starved mouse embryo and human fetus fibroblasts.* Cellular Signalling 12, 659-665.
Beck et al., (1994) *Expression of human placental alkaline phosphatase in Escherichia coli.* Protein Expression and Purification 5, 192-197.
Heimo et al., (1998) *Human placenta alkaline phosphatase: Expression in Pichia pastoris, purification and characterization of the enzyme.* Protein Expression and Purification 12, 85-92.

(Continued)

*Primary Examiner*—Jon Weber
*Assistant Examiner*—Rita Mitra
(74) *Attorney, Agent, or Firm*—Faegre & Benson LLP

(57) ABSTRACT

Methods for stimulating proliferation and inhibiting death of cells in the epidermis and dermis of wounded and non-wounded as well as transplanted mammalian skin and transplanted skin cell suspensions are described. The methods include the steps of administering to an area of wounded or non-wounded skin therapeutically effective amounts of $\alpha_1$-antitrypsin, alkaline phosphatase (such as placental alkaline phosphatase), transferrin, and $\alpha_1$-acid glycoprotein in compositions that contain at least two of these proteins, or their active derivatives, as the major active components. The compositions can be administered topically and/or by injection, or both. The invention also provides regimens for restoring or maintaining the strength and thickness of wounded, non-wounded and transplanted skin as well as developing new skin from skin cell suspensions comprising periodically administering one or more compositions topically and/or by injection.

39 Claims, 20 Drawing Sheets

OTHER PUBLICATIONS

Kozlenkov et al., (2002) *Function assignment to conserved residues in mammalian alkaline phosphatase*. J. Biol. Chem. 277, 22992-22999.

Carlevaro et al., (1997) *Transferrin promotes endothelial cell migration and invasion: Implication in cartilage neovascularization*. J. Cell. Biol. 136, 1375-1384.

Qian et al., (2002) *Targeted drug delivery via the transferrin receptor-mediated endocytosis pathway*. Pharmacol. Rev. 54, 561-587.

"Composition and Methods for Skin Rejuvination and Repair," U.S. Appl. No. 10/222,949, filed Aug. 16, 2002.

Tomiya et al., (2003) *Complex -type biantennary N-glycans of recombinant human transferring from Trichoplusia ni cells expressing mammalian β-1,4-galactotransferase and β-1,4-N-acetylglucosaminenyltransferase II*. Glycobiology 13, 23-24.

Pos et al., (1990) *Con A-nonreactive human $\alpha_1$-acid glycoprotein (AGP) is more effective in modulation of lymphocyte proliferation than Con A-reactive AGP serum variants*. Inflammation 14, 133-141.

Fournier et al., (2000) *Alpha-1-acid glycoprotein*. Biochim. Biophys. Acta 1482, 157-171.

Vasson et al., (1994), *Effects of alpha-1 acid glycoprotein on human polymorphonuclear neutrophils: influence of glycan microheterogeneity*. Clinica Chimica Acta 224, 65-71.

Williams et al., (1997) *$\alpha_1$-Acid glycoprotein reduces local and remote injuries after intestinal ischemia in the rat*. Am. J. Physiol. 273, G1031-G1035.

Stone et al., (1987) *Cloning and developmental regulation of $\alpha_1$-acid glycoprotein in swine*. Developmental Genetics 8, 295-304.

Durand et al., (1997) *Gene expression of a protein, JB70, related to rat $\alpha_1$-acid glycoprotein in Euglena gracilis*. Biochim. Biophys. Res. Commun. 234, 544-548.

Atemezem et al., (2001) *Human $\alpha_1$-acid glycoprotein binds to CCR5 expressed on the plasma membrane of human primary macrophages*. Biochem. J. 356, 121-128.

Sen et al., (2002) *Oxidant-induced vascular endothelial growth factor expression in human keratinocytes and cutaneous wound healing*. J. Biol. Chem. 277, 33284-33290.

Khanna et al., (2002) *Dermal wound healing properties of redox-active grape seed proanthocyanidins*. Free Radical Biol. Med. 33, 1089-1096.

Shi et al., (2000) *Supplemental dietary arginine enhances healing in normal but not inducible nitric oxide synthase knockout mice*. Surgery 128, 374-378.

Ashcroft et al., (2003) *Estrogen modulates cutaneous wound healing by downregulating macrophage migration inhibitory factor*. J. Clin. Invest. 111, 1309-1318.

Trif et al., (2001) *Liposomes as possible carriers for lactoferrin in the local treatment of inflammatory diseases*. Exp. Biol. Med. 226, 559-564.

Arthur et al., (1993) *The ethanolamine requirement of keratinocytes for growth is not due to defective synthesis of ethanolamine phosphoacylglycerols by the decarboxylation pathway*. Biochem, J. 293, 125-130.

He et al., (2003) *Progranulin is a mediator of the wound response*. Nature Medicine 9, 225-228.

Granoth et al. (2000) *VIP and the potent analog, stearyl-Nle$^{17}$-VIP, induce proliferation of keratinocytes*. FEBS Lett. 475, 78-83.

Oike et al., (2003) *Angiopoietin-related growth factor (AGF) promotes epidermal proliferation, remodeling, and regeneration*. Proc. Natl. Acad. Sci. USA 100, 9494-9499.

Cao et al., (2002) *Galectins-3 and -7, but not galectin-1, play a role in re-epithelization of wound*. J. Biol. Chem. 277, 42299-42305.

Trowbridge et al., (2002) *Dermatan sulfate binds and potentiates activity of keratinocyte growth factor (FGF-7)*. J. Biol. Chem. 277, 42815-42820.

Chang et al., (1992) *Human placenta alkaline phosphatase: An improved purification procedure and kinetic studies*. Eur. J. Biochem. 209, 241-247.

Chang et al., (1990) *Modification of human placental alkaline phosphatase by periodate-oxidized 1, $N^6$-ethenoadenosine monophosphate*. Biochem. J. 272, 683-690.

Boukamp et al., (1988) *Normal keratinization in a spontaneously immortalized aneuploid human keratinocyte cell line*. J. Cell Biol. 106, 761-771.

Carmichael et al., (1987) *Evaluation of a tetrazolium-based semiatumated colorimetric assay: Assessment of chemosensitivity testing*. Cancer Res. 47, 936-942.

Juhász et al., (1996) *Repopulation of Langerhans cells during wound healing in an experimental human skin/SCID mouse model*. Immunology Letters 52, 125-128.

Wankell et al., (2001) *Impaired wound healing in transgenic mice overexpressing the activin antagonist follistatin in the epidermis*. The EMBO J. 20, 5361-5372.

* cited by examiner

A

B

PROTEIN COMPOSITIONS FOR PROMOTING WOUND HEALING AND SKIN REGENERATION

REFERENCE TO RELATED APPLICATIONS

This application claims the benefit of U.S. provisional patent application Ser. No. 60/698,321 filed Jul. 12, 2005 and entitled "PROTEIN COMPOSITIONS FOR HEALING WOUNDS AND UNHEALTHY SKIN" which is hereby incorporated by reference in its entirety.

BACKGROUND

Recent remarkable advances in understanding the cellular and molecular mechanisms of wound repair have not yet led to similar advancements in wound care. An effective wound repair-promoting drug or composition would find multiple applications including healing of surgical wounds, accidental (burnt or cut) wounds, sunburns, or wounds generated by cosmetic surgeries. In addition, such agent(s) would also be expected to increase the efficacy of various skin grafting procedures as well as help to reduce skin damage induced by aging or environmental stresses.

Wound repair involves three major partially overlapping complex processes that follow a specific time sequence: inflammation, tissue formation, and tissue remodeling [Martin, P. (1997) *Wound healing—Aiming for perfect skin regeneration*. Science 276, 75-81]. These events are regulated by numerous growth factors and cytokines [Werner S. and Grose, R. (2003) *Regulation of wound healing by growth factors and cytokines*. Physiol. Rev. 10, 835-870]. Because of the complexity of these processes, application of a single growth factor does not seem to be sufficient to significantly promote wound healing. For example, platelet-derived growth factor (sold under the name of "Regenerex") was approved by FDA for wound healing application, but proved relatively ineffective. A probable reason for this is that platelet-derived growth factor stimulates only the proliferation of fibroblasts in the deeper dermis layer, and this may not be sufficient to significantly impact the proliferation of cells in the epidermis (keratinocytes).

Application of a mixture of growth factors would be another possibility to promote wound healing. However, most growth factors are short lived (rapidly degraded by proteases present in the wound fluid) and often counteract each other's effects or may be difficult to establish an optimal dose. For example, transforming growth factor-$\alpha$ and transforming growth factor-$\beta$ have stimulatory and inhibitory effects on keratinocyte proliferation, respectively [Werner S. and Grose, R. (2003) *Regulation of wound healing by growth factors and cytokines*. Physiol. Rev. 10, 835-870]. High-dose epidermal growth factor induces the production of transforming growth factor-$\beta$ and thereby inhibits proliferation of keratinocytes [Yamasaki, K., Toriu, N., Hanakawa, Y., Shirakata, Y., Sayama, K., Takayanagi, A., Ohtsubo, M., Gamou, S., Shimizu, N., Fujii, M., Miyazono, K, and Hashimoto, K. (2003) *Keratinocyte growth inhibition by high-dose epidermal growth factor is mediated by transforming growth factor $\beta$ autoinduction: A negative feedback mechanism for keratinocyte growth*. J. Invest. Dermatol. 120, 1030-1037]. Thus, it is difficult to establish an effective dose for epidermal growth factor. For these and other reasons, development of an effective growth factor mixture to promote wound healing has, so far, met with only limited success. In conclusion, there is still an unmet need to provide an agent or a mixture of agents that effectively promote(s) wound repair and restore(s) or maintain(s) the healthy structure of skin challenged by environmental stresses.

SUMMARY OF THE INVENTION

In view of the complexity of the wound healing process, significant effects require the sequential application of several agents that act at different steps with helping, rather than intervening with, each agent's effects. In this invention, four proteins are used in various compositions to promote wound healing and enhance the quality of skin. Each protein was selected because it has a partially different spectrum of cellular actions and each positively affects the non-chronic wound healing process in collaboration with the other proteins. Depending on the nature, size and location of the wound, compositions derived from these proteins can be enhanced by other agents that are known to positively affect the wound healing process.

The present invention provides various combinations of four proteins that enhance proliferation of human skin fibroblasts in vitro and in vivo as well as human and mouse epidermal cells in vivo. Three out of the four proteins, i.e. human $\alpha_1$-antitrypsin (AT), human placental alkaline phosphatase (PALP) and human transferrin (TF) enhance each other's effects on skin cell proliferation and survival, while the fourth protein, $\alpha_1$-acid glycoprotein is employed to reduce the level of inflammation. All four proteins may be used in various combinations. For example, some combinations include AT+PALP+TF or their active derivatives and PALP+TF+AGP or their active derivatives. These combinations may be used sequentially as part of one treatment regimen or may be used separately as independent treatments. Any other combination of these four proteins, containing a minimum of two of these proteins, may be applied.

The first protein is $\alpha_1$-antitrypsin (AT) which serves as a chemoattractant for the neutrophils while it prevents the destructive effects of neutrophil-derived elastase. In addition, AT stimulates proliferation of fibroblasts and epidermal cells. The second protein is a human alkaline phosphatase, such as placental alkaline phosphatase (PALP), which promotes cell survival and stimulates skin cell proliferation. Other human alkaline phosphatases such as intestinal, non-specific, and germ cell alkaline phosphatases may also be used. The third protein is transferrin (TF) which promotes proliferation and migration of endothelial cells. In addition, TF has anti-microbial effects based on its ability to strongly bind iron that is essential for the growth of bacteria and yeast. Finally, the fourth protein is $\alpha_1$-acid glycoprotein (AGP) which is one of the proteins that regulates the inflammation process.

The four proteins may be used in several different compositions using different treatment schedules. For example, in case of non-chronic wounds, two compositions may be used sequentially. The first composition may be composed of AT, TF and PALP and is used during the first three-four days of the wound care period. This composition will enhance some critically important mechanisms of inflammation (release of growth factor and cytokines) that are useful for wound healing, while it will decrease those activities (elastase and other protease activities) that are initially counter-productive. In addition, this composition will stimulate skin cell proliferation. Depending on the nature of additives and enhancers (for example, including conventional anti-bacterial agents), TF may not be included in the first composition. A second composition may be composed of TF, PALP and AGP and may be used 3-4 days after the application of the first composition. This composition is designed to decrease inflammation as well as promote proliferation and migration of skin cells including endothelial cells. Any other combination of these four protein components that includes at least two proteins or their active derivatives may also be feasible.

The present invention provides a method for stimulating the proliferation of cells in the dermis and epidermis in non-chronic wounds by sequential use of AT+PALP or TF+PALP or AT+PALP+TF or AT+PALP+TF+AGP compositions and then the PALP+TF+AGP or AT+PALP+TF+AGP compositions. Therapeutically effective amounts of these proteins or their derivatives may be administered topically to the wounded area. In one embodiment of the method, the skin is human skin. In another embodiment of the method, a physiologically compatible carrier and the proteins or their active derivatives are periodically administered to the skin in a given order.

The invention also provides a method to accelerate healing of chronic wounds, such as diabetic ulcer, or non-chronic wounds, by periodically administering by topical application to the skin a composition containing PALP+TF+AGP or their derivatives at therapeutically effective amounts. AT may be made part of this composition if the inflammation in the wounded tissue is not brought under control by other means. In case of diabetic patients, topical treatment for stimulation of proliferation and prevention of death of skin cells may be accompanied by simultaneous treatments with any of the available anti-diabetic medications.

Also provided by the invention is a method for stimulating proliferation and reducing death of cells in the epidermis and dermis of non-wounded skin that can be healthy or non-healthy (for example, aging) mammalian skin by compositions containing therapeutically effective amounts of AT, PALP, TF or AGP. Such compositions will contain at least two proteins that are dissolved or dispersed in physiologically compatible carriers and are administered either topically or via injection. Suitable compositions are TF+PALP, AT+PALP, TF+AT, AT+PALP+TF, or AT+PALP+TF+AGP or their active derivatives. In one embodiment the application is topical. In another embodiment the application is intradermal. In yet another embodiment of the method, the application may be an intravenous, subcutaneous, intramuscular, or intraperitoneal injection. In a further embodiment, topical and intradermal applications may be scheduled either simultaneously or sequentially.

The invention further provides a method for stimulating proliferation and reducing death of cells of transplanted skin, including a step of topically administering to an area of the transplanted skin therapeutically effective amounts of AT, PALP, TF or AGP in various combinations dissolved or dispersed in physiologically compatible carriers. Suitable compositions are TF+PALP, AT+PALP, TF+AT, AT+PALP+TF, and AT+PALP+TF+AGP or their active derivatives. In one embodiment the transplanted skin is human skin. In another embodiment of the method, the transplanted skin has been transplanted onto the human host. Another embodiment of the method includes a step of topically administering therapeutically effective amounts of protein combinations to an area of host skin that is adjacent to the transplanted skin. Yet another embodiment of the method includes a step of topically administering therapeutically effective amounts of protein combinations both to an area of host skin adjacent to the transplanted skin and directly to the transplanted skin.

The invention also provides a method for stimulating proliferation and reducing death of cells of transplanted skin by injecting to an area near the transplanted skin a composition comprising therapeutically effective amounts of AT, PALP, TF or AGP, or their active derivatives dissolved or dispersed in a physiologically acceptable carrier. Physiologically acceptable carrier may be 0.9 M sodium chloride (physiological saline).

The invention also provides a method for stimulating proliferation and reducing death of cells of both host and transplanted skin by combining topical applications and injection methods to administer the active composition(s) by one of the systemic routes or into or near the affected areas of host and transplanted skin.

Finally, the invention provides a method for stimulating proliferation and reducing death of transplanted skin cell suspensions by adding to such suspensions therapeutically effective amounts of AT, PALP, TF or AGP, or their active derivatives, in combinations that contain at least two of these proteins. Such method may or may not include additional topical treatments of the site of transplantation after initial stabilization of transplanted cells. Combinations of AT, PALP, TF and AGP in this embodiment may be applied by one of the injection methods used in the medical practice.

Compositions for topical applications are also provided by the invention. In one embodiment, the composition includes either *vaselinum flavum* or *vaselinum album* and amounts of the chosen proteins that are effective in stimulating proliferation and reducing death of cells in the dermis and epidermis of mammalian skin. In another embodiment, the composition essentially contains *vaselinum flavum* or *vaselinum album* as well as one of the following combinations of proteins or their active derivatives; TF+PALP, AT+PALP, TF+AT, AT+PALP+TF, PALP+TF+AGP, and AT+PALP+TF+AGP. In a further embodiment, the composition essentially contains *vaselinum cholesterinatum* and one of the following combinations of proteins or their active derivatives; TF+PALP, AT+PALP, TF+AT, AT+PALP+TF, and PALP+TF+AGP, and AT+PALP+TF+AGP. The same active protein compositions can be used for delivery via injection. The most suitable carrier for injected compositions is physiological saline.

BRIEF DESCRIPTION OF THE DRAWINGS

FIG. 13 is a digital image of a histological sample from transplanted human skin taken 6 days after immersing the skin into 65° C. water and treating twice with apo-TF (aTF; iron-free) alone dispersed in *vaselinum cholesterinatum*. aTF increased the influx of inflammatory cells into the dermis and induced the formation of new epidermis, but overall it was no more effective than PALP or PALP+AT.

DETAILED DESCRIPTION

Figure 1:
FIG. 1 is an image of a gel separation, demonstrating that the PALP used for the experiments shown in Table 2 as well as FIGS. 3B, 5, 7, 10, 11, 12, 15, 16, 17, 18, 19 and 20 was homogeneous or near homogeneous.

The experiments described herein demonstrate that, under several conditions, topically or intradermally applied protein compositions, chosen from AT, PALP, TF or AGP, promote survival and regeneration of cells both in the dermis and epidermis in mouse dorsal skin and in human skin transplanted onto mouse skin. Topical administration of the 4-protein composition induced formation of new layers in the epidermis in mouse skin. Intradermal application of the 4-protein composition enhanced formation of new layers in the epidermis both in the mouse and human skin. Topical administration of various compositions containing 2, 3 or 4 proteins promoted regeneration of both human epidermis and dermis after damaging the skin by exposing to hot water. These were also the compositions that most effectively stimulated proliferation of skin fibroblasts in vitro. These observations imply that some of the compositions containing 2 or 3 or 4 proteins can be used as active components of wound healing and skin care products. These products may repair the epidermal and dermal layers of wounded skin. They may also repair and prevent environmental stress-induced deterioration of skin structure in not visibly wounded (referred to as non-wounded herein) skin. Effective compositions that may be used sequentially or as mono-therapy are those that contain TF+PALP, AT+PALP, TF+AT, AT+PALP+TF, PALP+TF+AGP, and AT+PALP+TF+AGP. A suitable composition to heal chronic wounds may contain PALP+TF+AGP, although other combinations may also be feasible depending on other factors such as extent of inflammation, blood glucose level, etc.

Another therapeutic application described herein for compositions composed of AT, PALP, TF and AGP is to increase the success of skin grafting procedures by stimulating the proliferation and reducing the death of skin cells in host skin, transplanted skin and in skin cell suspensions.

The Active Components

One of the active components in the methods and compositions of the present invention is human $\alpha_1$-antitrypsin (AT), or an active derivative thereof. As used herein, the term "AT" and the phrase human AT are used interchangeably to refer to $\alpha_1$-antitrypsin. As used herein, active AT means the various isoforms of the human protein, or closely related mammalian proteins, and its/their glycosylated and non-glycosylated forms as well as peptides derived from these proteins that, when administered together with PALP and/or TF and/or AGP proteins, is effective to enhance the proliferation of skin cells and thereby effective to promote wound healing and increase the strength and thickness of both wounded and non-wounded skin.

AT belongs to the large family of serine protease inhibitors, or serpins, that act as irreversible silicide inhibitors of proteases [Janciauskiene, S. (2001) *Conformational properties of serine proteinase inhibitors (serpins) confer multiple pathophysiological roles*. Biochim. Biophys. Acta 1535, 221-235]. While AT is a particularly effective inhibitor of elastase, it also inhibits other proteases such as trypsin. AT deficiency, often caused by its oxidative damage in smokers, is causally related to emphysema due to the uncontrolled action of proteases in the lung.

In addition to function as a protease inhibitor, AT has also been shown to stimulate proliferation of various cell types [Perraud, F., Besnard, F., Labourdette, G. and Sensenbrenner, M. (1988) *Proliferation of rat astrocytes but not of oligodendrocytes, is stimulated in vitro by protease inhibitors*. Int. J. Devl. Neuroscience 6, 261-266; She, Q.-B., Mukherjee, J. J., Crilly, K. S. and Kiss, Z. (2000) $\alpha_1$-*Antitrypsin can increase insulin-induced mitogenesis in various fibroblast and epithelial cell lines*. FEBS Lett. 473, 33-36; Dabbagh, K., Laurent, G. J., Shock, A., Leoni, P., Papakrivopoulou, J. and Chambers, R. C. (2001) *Alpha-1-antitrypsin stimulates fibroblast proliferation and procollagen production and activates classical MAP kinase signaling pathways*. J. Cell. Physiol. 186, 73-81]. One reason for the inclusion of AT in a composition is its ability to stimulate the proliferation of skin cells.

In the wound, under inflammatory conditions, nitric oxide nitrosylates AT which exhibits significant antibacterial activity [Janciauskiene, S. (2001) *Conformational properties of serine proteinase inhibitors (serpins) confer multiple pathophysiological roles*. Biochim. Biophys. Acta 1535, 221-235]. In the wound, a portion of AT is also proteolitically degraded by gelatinase B (MMP-9) resulting in a cleaved form which acts as a potent chemoattractant for monocytes [Janciauskiene, S. (2001). *Conformational properties of serine proteinase inhibitors (serpins) confer multiple pathophysiological roles. Biochim. Biophys. Acta* 1535, 221-235]. Monocyte-derived cytokines are expected to enhance the strength of the inflammatory phase. These two useful activities added to the reasons to include AT in some of the compositions. Relatively pure AT is commercially available (for example, from Sigma-Aldrich), and it also can be highly purified from commercial PALP preparation which contains it as a significant contaminant. For the purpose of this application essentially pure AT, purified from commercial PALP preparation (Sigma-Aldrich) by a previously described method [She, Q.-B., Mukherjee, J. J., Crilly, K. S. and Kiss, Z. (2000) $\alpha_1$-*Antitrypsin can increase insulin-induced mitogenesis in various fibroblast and epithelial cell lines*. FEBS Lett. 473, 33-36] was used.

Relatively pure human AT, isolated from human plasma, can be purchased, for example, from Sigma-Aldrich (catalog number: A 9024). Essentially pure AT, purified from commercial human placental alkaline phosphatase preparations (from Sigma-Aldrich) that contain AT as a significant contaminant, were used for the invention. Purification of AT is described under "Examples". By implication, AT can be isolated in essentially pure form from human placenta. Placenta not only produces this protein [Bergman, D., Kadner, S. S., Cruz, M. R., Esterman, A. L., Tahery, M. M., Young, B. K. and Finlay, T. H. (1993) *Synthesis of $\alpha_1$-antichymotrypsin and $\alpha_1$-antitrypsin by human trophoblast*. Pediatric Res. 34, 312-317], but placenta-associated blood also is a rich source of AT.

Various protease enzymes can generate ~4-5 kDa carboxyl-terminal fragments of 36-44 residues from AT that serve as potent chemoattractants for monocytes. Instead of using only the intact AT, various compositions may contain one of these or other AT-derived fragments with or without the intact AT. Experts in the art can synthesize such peptides using solid phase chemistry or other conventional methods [Niemann, M. A., Bagott, J. E. and Miller, E. J. (1997) *Inhibition of human serine proteases by SPAAT, the C-terminal 44-residue peptide from $\alpha_1$-antitrypsin*. Biochim. Biophys. Acta 1340, 123-130].

The sequence of AT is known and the corresponding cDNA is available [Leicht, M., Long, G. L., Chandra, T., Kurachi, K., Kid, V. J., Mace, M. Jr., Davie, E. W. and Woo, S. L. C. (1982) *Sequence homology and structural comparison between the chromosomal human $\alpha_1$-antitrypsin and chicken ovalbumin genes*. Nature 297, 655-659; Long, G. L., Chandra, T., Woo, S. L. C., Davie, E. W. and Kurachi, K. (1984) *Complete Sequence of the cDNA from human $\alpha_1$-antitrypsin and the gene for the S. variant*. Biochemistry 23, 4828-4837]. Molecular biology techniques are available to produce recombinant forms of AT, mutated forms of AT [Kwon, K.-S., Kim, J., Shin, H. S. and Yu, M.-H. (1994) *Single amino acid substitutions of $\alpha_1$-antitrypsin that confer enhancement in thermal stability*. J. Biol. Chem. 269, 9627-9631], or the carboxyl-terminal fragment of AT, or any other fragment of AT [Kataoka, H., Uchino, H., Iwamura, T., Seiki, M., Nabeshima, K. and Koono, M. (1999) *Enhanced tumor growth and invasiveness in vivo by a carboxyl-* terminal fragment of $\alpha_1$-proteinase inhibitor generated by matrix metalloproteinases: A possible modulatory role in natural killer cytotoxicity. American J. Pathol. 154, 457-468]. These and similar techniques may be used to generate various active recombinant forms of AT and its derivatives.

The probability of significant toxic effects of AT via topical or intradermal application is very low, because AT is already a major protein in the human blood and these applications cannot possibly measurably increase its concentration in the circulation. However, even if a measurable increase in its blood concentration would occur, according to our present knowledge it would not be accompanied by any significant toxic effect. It should be noted that AT is an acute phase reactant, and its level during inflammation can increase 2-3 fold without causing any recognized side effect.

The stimulatory effects of AT on fibroblast proliferation in vitro is enhanced by pre-heating it at 65-75° C. for 30 min or at 41° C. for 21 hours [She, Q.-B., Mukherjee, J. J., Crilly, K. S. and Kiss, Z. (2000) $\alpha_1$-Antitrypsin can increase insulin-induced mitogenesis in various fibroblast and epithelial cell lines. FEBS Lett. 473, 33-36]. Pre-heating of AT also will enhance its stimulatory effects on skin cell proliferation in vivo. Thus, a step of heat-activation of AT may be included during the preparation of active compositions.

AT preparations that are commercially available contain impurities. Impure commercial AT preparations can be used as starting material to obtain homogeneous AT by successive chromatographic steps, as described in detail in Example 2. Impure AT preparations may also be used in formulating the compositions for use in the practice of the present invention, so long as the given composition comprises therapeutically effective amount of AT, and impurities are not toxic and do not interfere with the beneficial effects of the components.

A preparation containing human AT may also be obtained by extraction from placental tissue that synthesizes the protein during pregnancy. By way of example, a preparation may be obtained by butanol extraction of homogenized placenta. Other methods of extraction from placental tissue are also suitable.

Raw extracts or fractions derived from the blood or placenta that are not further enriched in AT by using physical concentration methods cannot be expected to have physiological effects similar to those observed for the preparation of sufficiently enriched or purified or homogenous AT. The main reason is that in the extracts or crude fractions the relative concentration of AT will be too low to expect a readily detectable effect in the skin.

Therefore, if blood- or placenta-derived AT preparation is to be used in the practice of the present invention, a raw extract or fraction should be treated to enrich the concentration of AT and obtain a purified preparation. A purified preparation will have a higher concentration of the active component than found in a raw tissue or blood extract. The term "purified" is used herein to encompass compositions that are obtained from a starting material by one or more purification steps (such as solvent extraction, column separation, chromatographic separation, etc.) that enhance the concentration of AT, relative to the starting material. The term "purified AT" should not be construed to connote absolute purity of the protein.

A further consideration in the practice of the invention is the degree of purity that is required for the use in wound healing and skin care compositions. An advantage of using a preparation comprising highly purified or homogeneous AT in the methods and treatment regiments of the present invention is that possible side effects caused by contaminating proteins will not likely be an issue. However, impure AT or AT that is purified but not homogeneous also can be used in the compositions described herein, so long as no adverse effects are observed. Since each additional purification step results in some loss of the protein, using a less pure AT material for the compositions would be more cost-effective. AT has not yet been used for stimulating wound repair, particularly not in the presence of the three other proteins as disclosed here.

The second active component in the methods and compositions of the present invention is placental alkaline phosphatase, or an active derivative thereof. As used herein, the term "PALP" refers to all alkaline phosphatases and is not limited to only placental alkaline phosphatase in order to make this application more readable to those in the art. Therefore, the term PALP as used herein refers to placental alkaline phosphatase as well as intestinal alkaline phosphatase, germ cell alkaline phosphatase, and tissue nonspecific alkaline phosphatase. Tissue nonspecific alkaline phosphatase can be found in bone, liver, and kidney.

Out of placental alkaline phosphatase, intestinal alkaline phosphatase, germ cell alkaline phosphatase, and tissue nonspecific alkaline phosphatase, only placental alkaline phosphatase stimulated fibroblast growth in vitro. At present it is not clear if stimulation of wound healing in vivo is entirely or only partly mediated via direct stimulation of skin cell proliferation. Some indirect mechanisms requiring alkaline phosphatase activity, for example local stimulation of growth factor production by fibroblasts or infiltrating immune cells may significantly contribute to the stimulatory effect of PALP on wound healing in vivo.

It has been observed that in vitro placental alkaline phosphatase, intestinal alkaline phosphatase and tissue nonspecific alkaline phosphatase all had similar stimulatory effects on DNA synthesis in embryonal mouse NIH fibroblasts in the presence of 2 mM calcium chloride (Z. Kiss, unpublished observations). In this context, it is important to note that in the wounded epidermis the extracellular concentration of calcium can easily reach 2 mM (instead of the more physiological 1.1 mM) or higher concentration. For these reasons, all alkaline phosphatases may at least partly mimic the stimulatory effects of placental alkaline phosphatase on wound healing in combination with one or more of AT, TF, and AGP.

Active PALP means the protein and its glycosylated and non-glycosylated forms as well as peptides derived from these proteins that, when administered together with AT and/or TF and/or AGP proteins, is effective to enhance the proliferation and reduce the death of skin cells and thereby promote wound healing and increase the strength and thickness of skin.

It has been reported that placental alkaline phosphatase one of the presently known four members of the alkaline phosphatase enzyme family [J. L. Millan, and W. H. Fishman (1995) *Biology of human alkaline phosphatases with special reference to cancer*. Critical Reviews in Clinical Sciences 32, 1-39], can enhance both the proliferation [Q.-B. She, J. J. Mukherjee, J.-S. Huang, K. S. Crilly, and Z. Kiss (2000) *Growth factor-like effects of placental alkaline phosphatase in human fetus and mouse embryo fibroblasts*. FEBS Letters, 468, 163-167] and survival [Q.-B. She, J. J. Mukherjee, T. Chung, and Z. Kiss (2000) *Placental alkaline phosphatase, insulin, and adenine nucleotides or adenosine synergistically promote long-term survival of serum-starved mouse embryo and human fetus fibroblasts*. Cellular Signalling 12, 659-665] of mouse embryo fibroblasts as well as fibroblast-like cells derived from the lung of human fetus. In a U.S.A. patent and a U.S.A. patent application, placental alkaline phosphatase, but not the presently known three other alkaline phosphatases, was shown to also enhance proliferation of human fibroblasts [U.S. Pat. No. 7,011,965, entitled "Compositions and Methods for Stimulating Wound Healing and Fibroblast Proliferation"; U.S. patent application Ser. No. 10/653,622, filed Sep. 2, 2003 and entitled "Use of Placental Alkaline Phosphatase to Promote Skin Cell Proliferation"].

In the methods of the present application PALP is used in novel combinations with other proteins that significantly add to its effects. For example, while PALP significantly protects cells against certain death-inducing environmental effects, such as nutrient deprivation-associated oxygen free radicals [Q.-B. She, J. J. Mukherjee, T. Chung, and Z. Kiss (2000) *Placental alkaline phosphatase, insulin, and adenine nucleotides or adenosine synergistically promote long-term survival of serum-starved mouse embryo and human fetus fibroblasts*. Cellular Signalling 12, 659-665], it is not known to promote, for example, endothelial cell migration (as TF does) or to promote deposition of cytokines at the wound site (as AT does). Unlike AGP, it is also not known to exert anti-inflammatory effects. This is why the proposed wound-healing regimen includes other proteins, in addition to PALP, that can elicit these events. For this application, PALP was highly purified from commercial (Sigma-Aldrich) PALP preparation by a method described earlier [Q.-B. She, J. J. Mukherjee, J.-S. Huang, K. S. Crilly, and Z. Kiss (2000) *Growth factor-like effects of placental alkaline phosphatase in human fetus and mouse embryo fibroblasts*. FEBS Letters, 468, 163-167]. In the experience of this inventor, in various PALP preparations purchased from Sigma-Aldrich PALP represents 5-15% of the total protein.

PALP enzymes hydrolyze phosphate-containing compounds at alkaline pH. Mature PALP is a dimer of two identical glycosylated subunits. Each subunit has an approximate molecular weight of 66 kDa, as determined by gel electophoresis.

While whole PALP enzyme in its native state exhibiting alkaline phosphatase activity may be used, a smaller fragment of the PALP enzyme may also exert a beneficial effect on the proliferation and survival of fibroblasts in vitro. For example, both digestion of PALP with the protease bromelain and elimination of alkaline phosphatase activity through mutation provided an active derivative that was effective in vitro [See, e.g., U.S. patent application Ser. No. 10/653,622]. Therefore, a smaller PALP-derived molecule devoid of alkaline phosphatase activity may be as active in vivo as the full-length PALP enzyme. Consequently, a smaller fragment of a PALP amino acid sequence may be synthesized or developed that demonstrates efficacy similar to that of native PALP. By way of example, modification of a PALP amino acid sequence, or a sequence of smaller PALP peptides, by exchanging amino acids at critical sites to yield an active derivative may even improve the beneficial effects of PALP in combination with the other proteins disclosed herein. Likewise, chemical or enzymatic changes in the level and position of glycosylation may maintain or enhance the effects of PALP or its derivatives. In the practice of the present invention, it is envisioned that modified PALP, smaller PALP-derived peptides, or modified PALP-derived peptides may be similarly effective or even more effective than the native PALP enzyme, and are each considered to be active derivatives.

Human PALP in solid form is available commercially from Sigma-Aldrich, St. Louis, Mo. (Sigma catalog number P3895; CAS Registry Number 9001-78-9). Another commercial source of human PALP is Calbiochem (San Diego, Calif.; catalog number 524604).

Human PALP, and particularly a smaller molecular mass active derivative, may also be obtained by chemical synthesis using conventional methods. For example, solid-phase synthesis techniques may be used to obtain PALP and particularly a smaller active derivative.

Recombinant methods to obtain quantities of PALP (or an active derivative) are also suitable. Since cDNA of PALP is available, recombinant protein can be produced by one of the many existing conventional methods for recombinant protein expression. PALP has been cloned and expressed in several cell lines [J. L. Millan, and W. H. Fishman (1995) *Biology of human alkaline phosphatases with special reference to cancer*. Critical Reviews in Clinical Sciences 32, 1-39]. Production of recombinant PALP by both bacteria [Beck, R. and Burtscher, H. (1994) *Expression of human placental alkaline phosphatase in Escherichia coli*. Protein Expression and Purification 5, 192-197] and yeast [Heimo, H., Palmu, K. and Suominen, I. (1998) *Human placenta alkaline phosphatase: Expression in Pichia pastoris, purification and characterization of the enzyme*. Protein Expression and Purification 12, 85-92] has also been reported.

Bacterial expression yields non-glycosylated PALP. So far there is no evidence that native glycosylated PALP and bacteria-produced PALP would have significantly different effects on cell proliferation. Thus, in the methods of the present invention native glycosylated PALP and its active derivatives as well as non-glycosylated PALP and its active derivatives can be used interchangeably.

Recombinant PALP for the present study was prepared by a method described recently [Kozlenkov, A., Manes, T., Hoylaerts, M. F. and Millan, J. L. (2002) *Function assignment to conserved residues in mammalian alkaline phosphatase*. J. Biol. Chem. 277, 22992-22999].

A PALP preparation that is commercially available contains impurities. Impure PALP preparations can be used as starting material to obtain homogeneous PALP by successive chromatographic steps, as described in detail in Example 1. Impure PALP preparations may also be used in formulating the compositions for use in the practice of the present invention, so long as the given composition comprises therapeutically effective amount of PALP, and impurities are not toxic and do not interfere with the beneficial effects of the components.

A preparation containing human PALP may also be obtained by extraction from placental tissue. Human placenta synthesizes the enzyme during pregnancy, so that toward the end of the third term the level of PALP in the placenta tissue and the maternal/fetal blood becomes very high. By way of example, a preparation may be obtained by butanol extraction of homogenized placenta. Other methods of extraction from placental tissue are also suitable.

Raw placental extracts that are not further enriched in PALP by using physical concentration methods cannot be expected to have physiological effects similar to those observed for the preparation of sufficiently enriched or purified or homogenous PALP, for at least two reasons. First, the relative concentration of PALP in an extract will be too low to expect a readily detectable effect in the skin. Second, raw placental extracts contain not only many different proteins but also other kinds of compounds, such as many lipids, proteolipids, carbohydrates, metals, vitamins, and the like.

Therefore, if placenta-derived PALP preparation is to be used in the practice of the present invention, a raw extract should be treated to enrich the concentration of PALP and obtain a purified preparation. A purified preparation will have a higher concentration of the active component than found in a raw tissue extract, such as a raw placental extract. The term "purified" is used herein to encompass compositions that are obtained from a starting material by one or more purification steps (such as solvent extraction, centrifugation, column separation, chromatographic separation, etc.) that enrich the concentration of PALP, relative to the starting material. The term "purified" should not be construed to connote absolute purity.

A further consideration in the practice of the invention is the degree of purity that is required for the use in wound healing and skin care compositions. An advantage of using a preparation comprising highly purified or homogeneous PALP in the methods and treatment regiments of the present invention is that possible side effects caused by contaminating proteins will not likely be an issue. However, impure PALP or PALP that is purified but not homogeneous also can be used in the compositions described herein, so long as no adverse effects are observed. Since each additional purification step results in significant loss of the protein, using a less pure PALP material for the compositions would be more cost-effective.

The stimulatory effects of PALP on fibroblast proliferation in vitro is enhanced by pre-heating it at 65-75° C. for 30 min [Q.-B. She, J. J. Mukherjee, J.-S. Huang, K. S. Crilly, and Z. Kiss (2000) *Growth factor-like effects of placental alkaline phosphatase in human fetus and mouse embryo fibroblasts*. FEBS Letters, 468, 163-167]. Pre-heating of PALP prior to making the composition or pre-heating of the PALP-containing composition at 65-75° C. may also result in enhanced stimulation of skin cell proliferation in vivo. Thus, a step of heat-activation of PALP or PALP-containing compositions may be included during the preparation of final active compositions.

TF, the third potential component of wound healing and skin care compositions, is also a glycoprotein with an approximate molecular weight of 80 kDa. Its major function is to carry iron from the sites of intake into the systemic circulation to the cells and tissues. However, TF also serves as a growth factor for many cell types; for this reason, it is a standard component of several growth media used for cell culture. Whether the growth factor effects of TF are always mediated by iron or not is presently unclear. TF also promotes migration of endothelial cells [Carlevaro, M. F., Albini, A., Ribatti, D., Gentili, C., Benelli, R., Cermelli, S., Cancedda, R. and Cancedda, F. D. (1997) *Transferrin promotes endothelial cell migration and invasion: Implication in cartilage neovascularization*. J. Cell. Biol. 136, 1375-1384]. Thus, by simultaneous stimulation of skin cell proliferation and the vascularization process, TF significantly adds to the effects of AT and PALP on wound healing.

The structure and biological effects of TF as well as the properties of transferrin receptor have recently been reviewed [Qian, Z. M., Li, H., Sun, H. and Ho, K. (2002) *Targeted drug delivery via the transferrin receptor-mediated endocytosis pathway*. Pharmacol. Rev. 54, 561-587].

In several patent applications and patents, TF has been listed as a minor component of complex mixtures that may add to the effects of major promoters of skin rejuvenation and repair, without either specifying or directly proving such role [U.S. patent application Ser. No. 222,949, filed Apr. 10, 2003 and entitled "Composition and Methods for Skin Rejuvenation and Repair"; U.S. Pat. No. 5,461,030, issued Oct. 24, 1995 and titled "Compositions and Methods for Enhancing Wound healing"; U.S. Pat. No. 5,591,709, issued Jan. 7, 1997 and entitled "Compositions and Methods for Treating Wounds"; U.S. Pat. No. 5,556,645, issued Sep. 17, 1996 and entitled "Methods of Enhancing Wound Healing and Tissue Repair"; U.S. Pat. No. 4,347,841, issued Sep. 7, 1982 and titled "Biological Wound Covering and Method for Producing Same"]. TF has not been used to treat wounded or non-wounded skin alone or in combination with any of the three other proteins mentioned here, i.e. AT, PALP, or AGP.

As used herein, the term "TF" and the phrase "human TF" are used interchangeably to refer to transferrin. As used herein, active TF means the human protein, or closely related mammalian proteins, and its/their glycosylated and non-glycosylated forms as well as peptides derived from these proteins that, when administered together with AT and/or PALP and/or AGP proteins, is effective to enhance the proliferation of skin cells thereby promoting wound healing and increasing the strength and thickness of skin.

For these studies, essentially iron-free human Apo-TF (aTF) and iron-containing (iron content: 1100-1600 µg per 1-g protein) human holo-TF (hTF), both at least 97-98% pure, were purchased from Sigma-Aldrich (catalog numbers T 1147 and T 4132, respectively, according to the 2004/2005 Sigma Catalog). Because TF is a major component of human blood, and placenta always contains significant volume of blood, the placenta tissue is also a potential source for the isolation of this protein. Chromatographic separation methods are available for the purification of TF. For example, it is possible to enrich TF, along with some other glycoproteins, using a so called Concanavalin-A-Sepharose column, which separates glycoproteins based on their ability to interact with lectins such as Concanavalin-A. This step is then followed by other column chromatography methods, such as size-exclusion chromatography, to separate glycoproteins from each other. These techniques are well within the reach of expertise of experts in the art.

The sequence of human TF (which has approximately 10 variants) is known and the corresponding cDNA is available. This allows expression of original TF or its point and deletion mutants in any cell line of choice, for example in insect cells [Tomiya, N., Howe, D., Aumiller, J. J., Pathak, M., Park, J., Palter, K. B., Jarvis, D. L., Betenbaugh, M. J. and Lee, Y. C. (2003) *Complex-type biantennary N-glycans of recombinant human transferring from Trichoplusia ni cells expressing mammalian β-1,4-galactotransferase and β-1,4-N-acetylglucosaminenyltransfe II*. Glycobiology 13, 23-34]. These and similar techniques may be used to generate, at larger scale, various active recombinant forms of TF and its derivatives.

The probability of significant toxic effects of TF via topical or intradermal application is very low, because TF is already a major protein in the human blood and these applications cannot possibly measurably increase its concentration in the circulation. A sustained significant increase in its blood concentration, however, could offset the required balance of iron metabolism that may result in negative physiological consequences. However, a significant increase in blood TF observed during acute phase reactions has not been shown to cause detectable side effects.

The stimulatory effects of TF on fibroblast proliferation in vitro are not altered by pre-heating it at 65-75° C. for 30 min. Thus, pre-heating of TF-containing compositions to enhance the effects of other components, such as AT and PALP, will not alter the stimulatory effects of TF.

Most TF preparations that are commercially available contain only minor impurities comprising only 2-3% of the total protein. These commercial TF preparations can be further purified by available methods to obtain homogeneous TF by successive chromatographic steps. TF preparations with relatively minor impurities may also be used in formulating the compositions for use in the practice of the present invention, so long as the given composition comprises therapeutically effective amount of TF, and impurities are not toxic and do not interfere with the beneficial effects of the components.

Since TF is a major blood protein, and placenta tissue contains a significant volume of blood, human AT may also be obtained by extraction from placental tissue. By way of example, a TF preparation may be obtained by butanol extraction of homogenized placenta. Other methods of extraction from placental tissue are also suitable.

Raw extracts or fractions derived from the blood or placenta that are not further enriched in TF by using physical concentration methods cannot be expected to have physiological effects similar to those observed for the preparation of sufficiently enriched or purified or homogenous TF. The main reason is that in the extracts or crude fractions the relative concentration of TF will be too low to expect a readily detectable effect in the skin.

Therefore, if blood- or placenta-derived TF preparation is to be used in the practice of the present invention, a raw extract or fraction should be treated to enrich the concentration of TF and obtain a purified preparation. A purified preparation will have a higher concentration of the active component than found in a raw tissue or blood extract. The term "purified" is used herein to encompass compositions that are obtained from a starting material by one or more purification steps (such as solvent extraction, column separation, chromatographic separation, etc.) that enrich the concentration of TF, relative to the starting material. The term "purified TF" should not be construed to connote absolute purity of the protein.

A further consideration in the practice of the invention is the degree of purity that is required for the use in wound healing and skin care compositions. An advantage of using a preparation comprising highly purified or homogeneous TF in the methods and treatment regiments of the present invention is that possible side effects caused by contaminating proteins will not likely be an issue. However, impure TF or TF that is purified but not homogeneous also can be used in the compositions described herein, as long as no adverse effects are observed. Considering that every consecutive purification step, either using blood or placenta as starting material, results in some loss of the protein, using a less pure than homogeneous TF material for the compositions may be more cost-effective.

TF may contain iron or may be iron-free. Since both iron-free (aTF) and iron-containing (hTF) had similar stimulatory effects on fibroblast proliferation in the Examples, these two types of TF preparations may have similar effects on wound healing. Therefore, both iron-free and iron-containing TF, may be used in the methods of the present invention.

AGP ($\alpha_1$-acid glycoprotein or orosomucoid) is the fourth potential component of the wound healing and skin care compositions. Each molecule of native AGP contains five N-linked complex-type glycans. In normal serum, three differently glycosylated molecular forms of AGP are present, which can be detected by concanavalin A (Con A)-Sepharose chromatography. Molecular forms of AGP that have the greatest inhibitory effects on lymphocyte proliferation are the most abundant in normal serum [Pos, O., Oostendorp, R. A. J., Van der Stelt, M. E., Scheper, R. J. and Van Duk, W. (1990) *Con A-nonreactive human $\alpha_1$-acid glycoprotein (AGP) is more effective in modulation of lymphocyte proliferation than Con A-reactive AGP serum variants*. Inflammation 14, 133-141].

AGP ($\alpha_1$-acid glycoprotein or orosomucoid) is an acidic 41-43-kDa glycoprotein with a very high carbohydrate content of up to 45%. This protein is considered as a natural anti-inflammatory protein [Fournier, T., Medjoubi-N, N. and Porquet, D. (2000) *Alpha-1-acid glycoprotein*. Biochim. Biophys. Acta 1482, 157-171]; this is the major reason why it was considered to be part of the present wound healing compositions. The anti-inflammatory effects of AGP are due to its ability to reduce extravasation of leukocytes into the surrounding tissue (in the present case into the wounded/healing area) [Fournier, T., Medjoubi-N, N. and Porquet, D. (2000) *Alpha-1-acid glycoprotein*. Biochim. Biophys. Acta 1482, 157-171] and to inhibit the functions of polymorphonuclear neutrophils including chemotactic response and superoxide anion generation [Vasson, M. P., Roch-Arveiller, M., Couderc, R., Baguet, J. C. and Raichvarg, D. (1994) *Effects of alpha-1 acid glycoprotein on human polymorphonuclear neutrophils: influence of glycan microheterogeneity*. Clinica Chimica Acta 224, 65-71]. In line with these findings, AGP was shown to inhibit both complement- and neutrophil-mediated injuries [Williams, J. P., Weiser, M. R., Pechet, T. T. V., Kobzik, L., Moore, F. D. Jr. and Hechtman, H. B. (1997) $\alpha_1$-*Acid glycoprotein reduces local and remote injuries after intestinal ischemia in the rat*. Am. J. Physiol. 273, G1031-G1035].

Based on its anti-inflammatory properties, in case of non-chronic wounds, AGP is included, for example, in a composition that is used several days after the injury. This is when a decrease in the level of inflammation is desired in order to facilitate progression of the wound healing process. In case of chronic wounds, when inflammation probably needs to be controlled, AGP may be included in the wound healer composition from the start.

As used herein, the term "AGP" and the phrase "human AGP" are used interchangeably to refer to $\alpha_1$-acid glycoprotein. As used herein, active AGP means the human protein, or closely related mammalian proteins, and its/their variously glycosylated and non-glycosylated forms as well as peptides derived from these proteins that, when administered together with AT and/or TF and/or AGP proteins, is effective to enhance the proliferation and reduce the death of skin cells thereby promoting wound healing and increasing the strength and thickness of skin.

Essentially pure human AGP, isolated from human blood, is available from Sigma-Aldrich; this is the preparation that was used for the application (catalog number: G 9885 in 2004/2005 Sigma Catalog). Considering that AGP is a major protein in the human blood and that placenta tissue contains significant volume of blood, placenta can be a source for the isolation of AGP. Practically very similar extraction and chromatography methods can be used for the isolation of AGP from placenta that was indicated above for TF.

AGP, and particularly its smaller molecular mass active derivatives, may also be obtained by chemical synthesis using conventional methods. For example, solid-phase synthesis techniques may be used to obtain AGP or an active derivative.

Recombinant methods to obtain quantities of AGP (or active derivatives) are also suitable. The sequence of AGP from human and several mammalian species is known and the corresponding cDNAs are available; sequence homologies among the human, rat and porcine AGP proteins have been published [Stone, R. T. and Maurer, R. A. (1987) *Cloning and developmental regulation of $\alpha_1$-acid glycoprotein in swine*. Developmental Genetics 8, 295-304]. Accordingly, recombinant human or mammalian protein or their various molecular forms can be produced by one of the many existing conventional methods for recombinant protein expression as demonstrated, for example, in [Williams, J. P., Weiser, M. R., Pechet, T. T. V., Kobzik, L., Moore, F. D. Jr. and Hechtman, H. B. (1997) $\alpha_1$-*Acid glycoprotein reduces local and remote injuries after intestinal ischemia in the rat*. Am. J. Physiol. 273, G1031-G1035]. Production of recombinant wild type or mutant AGP or its derivative by bacteria, yeast, insect cells or mammalian cells is feasible by available methods.

Recently, production of an AGP-like protein, named JB70, was described in the alga *Euglena gracilis* [Durand, G., Delranc, C., Bonaly, J., Chacun, H., Porquet, D. and Barque, J.-P. (1997) *Gene expression of a protein, JB70, related to rat $\alpha_1$-acid glycoprotein in Euglena gracilis*. Biochim. Biophys. Res. Commun. 234, 544-548]. This is a strong indication that alga has the enzyme apparatus to synthesize and glycosylate human AGP once the human gene is introduced into the alga. This opens the possibility to use this alga for large-scale production of human AGP.

There is evidence that the biological effects of AGP depend on the level of glycosylation. Thus, in the methods of the present invention, the term "AGP" includes any non-glycosylated and glycosylated forms of AGP.

The human AGP preparation that is isolated from human plasma and is commercially available from Sigma-Aldrich does not contain detectable amounts of impurities as determined by SDS gel electrophoresis (Z. Kiss, unpublished data). However, impure AGP preparations may also be used in formulating the compositions for use in the practice of the present invention, so long as the given composition comprises therapeutically effective amount of AGP, and impurities are not toxic and do not interfere with the beneficial effects of the components.

A preparation containing human AGP may also be obtained by extraction from placental tissue due to its high concentration in the placenta's blood supply. By way of example, a preparation may be obtained by butanol extraction of homogenized placenta. Other methods of extraction from placental tissue are also suitable.

Raw extracts derived from the blood or placenta that are not further enriched in AGP by using physical concentration methods cannot be expected to have physiological effects similar to those observed for the preparation of sufficiently enriched or purified or homogenous AGP. The relative concentration of AGP in an extract would be too low to expect a readily detectable effect in the skin.

Therefore, if blood- or placenta-derived AGP preparation is to be used in the practice of the present invention, a raw extract should be treated to enrich the concentration of AGP and obtain a purified preparation. A purified preparation will have a higher concentration of the active component than found in a raw tissue extract, such as a raw placental extract. The term "purified" is used herein to encompass compositions that are obtained from a starting material by one or more purification steps (such as solvent extraction, centrifugation, column separation, chromatographic separation, etc.) that enrich the concentration of AGP, relative to the starting material. The term "purified" should not be construed to connote absolute purity.

A further consideration in the practice of the invention is the degree of purity of AGP that its use in wound healing and skin care compositions requires. An advantage of using a preparation comprising highly purified or homogeneous AGP in the methods and treatment regiments of the present invention is that possible side effects caused by contaminating proteins will not likely be an issue. However, impure AGP or AGP that is purified but not homogeneous also can be used in the compositions described herein, so long as no adverse effects are observed. Since each additional purification step results in some loss of the protein, using a less pure AGP material for the compositions could be more cost-effective.

Pre-heating at 65-75° C. for 30 min is not known to affect the biological effects of AGP. Only its complete denaturation by heating at 100° C. for 10 min causes significant decrease in its biological effects [Atezem, A., Mbemba, E., Vassy, R., Slimany, H., Saffar, L. and Gattegno, L. (2001) *Human $\alpha_1$-acid glycoprotein binds to CCR5 expressed on the plasma membrane of human primary macrophages*. Biochem. J. 356, 121-128]. Thus, a step of heat-treatment (at 65-75° C. for 30 min) of compositions to enhance the activities of PALP and AT is not likely to decrease the biological effects of AGP.

Others have not yet used AGP, alone or in combination with the three other proteins mentioned here, to treat either wounded or non-wounded skin.

Compositions made from the four basic protein constituents have multiple applications. The list includes healing of surgical wounds, accidental (burnt or cut) wounds, sunburns, or wounds generated by cosmetic surgeries, increasing the efficacy of various skin or skin cell grafting procedures, and help reducing skin damage induced by aging or environmental stresses. Many additives and "enhancing" agents can be used to further promote the effects of these four protein components.

Compositions for Topical Application

The present invention includes methods for stimulating proliferation and reducing death of skin cells, and methods for restoring or maintaining the strength and thickness of the wounded as well as non-wounded skin by topically applying protein-containing compositions. Any composition contains at least two of the following four proteins or their active derivatives; AT, PALP, TF or AGP. In any composition for administration to a human, the carrier should be a physiologically compatible or acceptable carrier.

For topical application, appropriate forms of compositions include, for example, creams, gels, lotions, unguents, emollients, colloidal dispersions, suspensions, emulsions, oils, sprays, foams, mousses, and the like. Compositions suitable for topical application may also include, for example, liposomal carriers made up of lipids or special detergents. The proteins may also be linked to nanoparticles and applied to the skin in an acceptable carrier such as those listed above. Nanoparticle-bound proteins may provide a more localized and sustained response because they are less diffusible than proteins suspended in the above carriers in the absence of nanoparticles.

Compositions suitable for topical application in the practice of the present invention generally include two, three, or all four of the active proteins as minor ingredients, and the physiologically compatible carrier as a major ingredient. In some embodiments, the compositions may include one or more additives or enhancers, such as preservatives, biologically active compounds with positive effects on skin cells, buffers, moisture-control compounds, or antibiotics, for example. In other embodiments, the composition essentially contains the carrier and the active components selected from AT, PALP, TF or AGP. As used here, the phrase "essentially contains" means that the given composition has no other ingredient, other than the recited active protein components.

A carrier may be in any form appropriate for topical application to the skin. Any physiologically compatible carrier in which the active components are at least minimally soluble is suitable for topical compositions of the present invention. A physiologically acceptable carrier is one that is non-toxic, does not elicit an adverse physical reaction upon administration, and in which the active components are sufficiently soluble so that the composition can provide an effective amount of each of the active component. The carrier should also provide the composition an appropriate consistency for topical administration and should be capable of achieving proper distribution of the active component to the treated tissue.

Suitable carriers generally include, for example, water, acetone, ethanol, ethylene glycol, propylene glycol, butane-1,3-diol, isopropyl myristate, isopropyl palmitate, mineral oil, mixtures thereof and the like. Buffered solutions can also serve as carriers.

In some embodiments, the topical composition is a gel. The gel may include as a carrier methylcellulose, sepharose, agar, vaseline or petrolatum, agarose, gelatin, dextran, dextranpolyethylene, polyhydroxyethylmethacrylate, hydrophilic cellulose polymer, polyethylene glycol, polyvinylpyrrolidine, amylose, polyethyleneoxide, calcium alginate or combination thereof. By way of example, the selected active components can be incorporated into sterile 3% by weight methyl cellulose gel, 1% by weight agarose gel, 4% by weight gelatin gel, or 1 to 3% by weight calcium alginate. Experts in the art will recognize how to vary these components to obtain sustained release and sustained presence of active components of the invention.

Gels of more complex compositions can be formulated. In some embodiments, the carrier includes *vaselinum flavum* (yellow petrolatum), *vaselinum album* (white petrolatum), or *vaselinum cholesterinatum*. Commercially available *vaselinum cholesterinatum* consists of about 1.5 wt.-% cholesterol, about 5.0 wt.-% cerae lanae, and about 93.5 wt.-% *vaselinum flavum*.

Additives or enhancers may be included in the topical compositions. The criterion for using an additive is that it increases, or at least does not significantly impair, the effectiveness of the active components in achieving the desired beneficial effect. Additives or enhancers in compositions for topical applications may include various ingredients, for example, preservatives (such as parabens, quaternary ammonium compounds, alcohols, phenols, essential oils and the like), buffers, antioxidants (such as vitamin E), antimicrobials, vitamins, nutrients (such as essential and non-essential amino acids, choline, inositol, minerals, trace metals, salts, nucleosides, purines, pyrimidines, monosaccharides, dissacharides, carbohydrates) and moisture-control agents (such as glycerine, propylene glycol, and the like). Other potential additives include, for example, analgesics, anesthetics, anti-acne agents, anti-dermatitis agents, anti-puritic agents, anti-inflammatory agents, anti-hyperkeratolytic agents, antiperspirants, anti-psoriatic agents, anti-seborrheic agents, anti-aging agents (such as retinoids including vitamin A), anti-wrinkle agents, anti-lightening agents, depigmenting agents, corticosteroids, additional tanning agents or hormones. Other additives may include, for example, colorants, sunscreens, emulsion stabilizers, preservatives, fragrance, humectants, waterproofing agents, viscosity modifying agents and the like.

One class of enhancers is represented by oxidants, such as hydrogen peroxide [Sen, C. K., Khanna, S., Babior, B. M., Hunt, T. K., Ellison, E. C. and Roy, S. (2002) *Oxidant-induced vascular endothelial growth factor expression in human keratinocytes and cutaneous wound healing*. J. Biol. Chem. 277, 33284-33290] and agents that act via oxidants such as, for example, grape seed proanthocyanidin extract [Khanna, S., Venojarvi, M., Roy, S., Sharma, N., Trikha, P., Bagchi, D., Bagchi, M. and Sen, C. K. (2002) *Dermal wound healing properties of redox-active grape seed proanthocyanidins*. Free Radical Biol. Med. 33, 1089-1096] and arginin, a substrate for nitric oxide generation [Shi, H. P., Efron, D. T., Most, D., Tantry, U. S. and Barbul, A. (2000) *Supplemental dietary arginine enhances wound healing in normal but not inducible nitric oxide synthase knockout mice*. Surgery 128, 374-378]. There are many other agents that can enhance the level oxidants in the skin.

Another class of enhancers is represented by agents that can reduce inflammation such as, for example, estrogen [Ashcroft, G. S., Mills, S. J., Lei, K., Gibbons, L., Jeong, M.-J., Taniguchi, M., Burow, M., Horan, M. A., Wahl, S. M. and Nakayama, T. (2003) *Estrogen modulates cutaneous wound healing by downregulating macrophage migration inhibitory factor*. J. Clin. Invest. 111, 1309-1318] and lactoferrin [Trif, M., Guillen, C., Vaughan, D. M., Telfer, J. M., Brewer, J. M., Roseanu, A. and Brock, J. H. (2001) *Liposomes as possible carriers for lactoferrin in the local treatment of inflammatory diseases*. Exp. Biol. Med. 226, 559-564].

An additional class of enhancers is represented by agents that have not yet been proven to efficiently promote in vivo wound healing on their own, but they have positive effects on the proliferation and survival of skin cells; therefore, they are expected to increase the effects of the active protein components described in the invention. The non-limiting list includes the following agents: (a) ethanolamine as well as ethanolamine derivatives such as monomethylethanolamine and dimethylethanolamine, which is required for proliferation of keratinocytes [Arthur, G. and Lu, X. (1993) *The ethanolamine requirement of keratinocytes for growth is not due to defective synthesis of ethanolamine phosphoacylglycerols by the decarboxylation pathway*. Biochem, J. 293, 125-130] (b) zinc and calcium that are required for the optimal effects of PALP on cell proliferation [Q.-B. She, J. J. Mukherjee, J.-S. Huang, K. S. Crilly, and Z. Kiss (2000) *Growth factor-like effects of placental alkaline phosphatase in human fetus and mouse embryo fibroblasts*. FEBS Letters, 468, 163-167], (c) growth regulatory agents including progranulin [He, Z., Ong, C. H. P., Halper, J. and Bateman, A. (2003) *Progranulin is a mediator of the wound response*. Nature Medicine 9, 225-228], vasoactive intesinal polypeptide [Granoth, R., Fridkin, M and Gozes, I. (2000) *VIP and the potent analog stearyl-Nle$^{17}$-VIP, induce proliferation of keratinocytes*. FEBS Lett. 475, 78-83], angiopoietin-related growth factor [Oike, Y., Yasunaga, K., Ito, Y., Matsumoto, S.-I., Maekawa, H., Morisada, T., Arai, F., Nakagata, N., Takeya, M., Masuho, Y. and Suda, T. (2003) *Angiopoietin-related growth factor (AGF) promotes epidermal proliferation remodeling and regeneration*. Proc. Natl. Acad. Sci. USA 100, 9494-9499], galectins-3 and -7 [Cao, Z., Said, N., Amin, S., Wu, H. K., Bruce, A., Garate, M., Hsu, D. K., Kuwabara, I., Liu, F.-T. and Panjwani, N. (2002) *Galectins-3 and -7, but not galectin-1, play a role in re-epithelization of wound*. J. Biol. Chem. 277, 42299-42305], dermatan sulfate [Trobridge, J. M., Rudisill, J. A., Ron, D. and Gallo, R. L. (2002) *Dermatan sulfate binds and potentiates activity of keratinocyte growth factor (FGF-7)*. J. Biol. Chem. 277, 42815-42820], and prostaglandin, (d) growth factors such as platelet-derived growth factor, transforming growth factor-β, epidermal growth factor, fibroblast growth factor, growth hormone, erythropoietin, hematopoietin, cytokines, insulin, insulin-like growth factor 1, vascular endothelial growth factor, granulocyte macrophage colony stimulating factor, keratinocyte growth factor that are well known to positively influence proliferation and survival of skin cells, and (e) wound repair promoters as hyaluronic acid, fibronectin, laminin, collagen, elastin, tenasin, glycosamineglycans, proteoglycans, and integrins.

In certain embodiments, the composition includes a penetration-enhancing additive that enhances penetration of the protein components into the skin. Many conventional penetration enhancers are suitable in the practice of the invention. Non-limiting examples of suitable penetration enhancers include: sulfoxides such as dimethyl sulfoxide (DMSO); alcohols such as ethanol; polyols such as propylene glycol; surfactants such as sodium lauryl sulfate, lecithin, docusate sodium, and polysorbates; fatty acids such as lauric acid, myristic acid, palmitic acid, mineral oil, and stearic acid; esters such as isopropyl palmitate and isopropyl myristate; and amide such as urea.

Compositions for topical administration can be made using any number of suitable techniques. For example, a carrier, a preparation comprising two or more active components, and any optional additives and enhancers can be mixed together using a commercial mixer to form a suspension, gel, solution or the like. Conventional methods known in the art are suitable. The compositions can be additionally processed before and after formulation. Sterilization, for example, can be conducted individually by filter sterilization, while the whole composition can be irradiated or heat-treated or the like. Conventional methods for conducting these steps are known.

Both purified proteins and homogeneous proteins obtained from blood or placental extracts can be used as the active components in the compositions described herein. The less pure the protein preparations are, proportionally more of the protein preparations must be used for the given topical composition in order to provide effective amounts of the active components. Alternatively, preparations containing synthetic proteins or their active derivatives, or recombinant proteins or their active derivatives, can be employed as active components.

Alternatively, all four proteins may be isolated from the same placenta tissue. This is feasible, because each protein is present in the placenta. Since each protein is a glycoprotein, the isolation procedure may be simplified. For example, if concanavalin A-reactive proteins have full effects in each case, then a concanavalin A-Sepharose column, which is commercially available, is suitable to separate the four proteins, along with other glycoproteins, from the majority of proteins that are not glycoproteins. Additional known chromatography steps are available to use the concentrated glycoprotein fractions to separate the four protein from each other as demonstrated for PALP and AT in Example 1 and Example 2, respectively.

In one embodiment, the composition is suitable to treat non-chronic wounds, chronic wounds, transplanted skin, transplanted skin cell suspension, and non-wounded skin and comprises therapeutically effective amounts of PALP and TF or their active derivatives thereof. The term "therapeutically effective amount" in this specification, as well as the claims, indicates a dosage that is effective in (a) enhancing proliferation and reducing death of keratinocytes and/or fibroblasts, (b) promoting healing of wounds, (c) restoring or maintaining the strength or thickness of non-wounded (for example, aging) skin, or (d) increasing or decreasing the influx of inflammatory cells into the treated skin area depending on the stage of healing process. A therapeutically effective amount of an active protein component may vary based on the number of active protein components in the composition, the needs or tolerance of the individual subject, the degree to which the ability of keratinocytes and fibroblasts to proliferate has degenerated, the degree to which strength or thickness of the subject's skin has deteriorated, or other criteria evident to one of ordinary skill in the art. "An active protein component" is defined as the full-length glycosylated or non-glycosylated molecules of AT, PALP, TF, or AGP or their active derivatives.

In another embodiment, the composition is specifically suitable to treat non-chronic wounds and/or skin transplants during the first few days of healing and comprises therapeutically effective amounts of AT and PALP or their active derivatives.

In still another embodiment, the composition is also suitable to treat non-chronic wounds or skin transplants during the first few days of healing and comprises therapeutically effective amounts of TF and PALP or their active derivatives.

In a different embodiment, the composition is also suitable to treat non-chronic wounds or skin transplants during the first few days of healing and comprises therapeutically effective amounts of TF and AT or their active derivatives.

In yet another embodiment, the composition is specifically suitable to treat non-chronic wounds and/or transplanted skin during the first few days of healing and comprises therapeutically effective amounts of AT, PALP and TF or their active derivatives.

In some embodiments, the composition is suitable to treat non-chronic wounds, chronic wounds, skin transplants and non-wounded skin and comprises therapeutically effective amounts of PALP, TF and AGP or their active derivatives.

In another embodiment, the composition is suitable to treat non-chronic wounds or skin transplants during the whole healing or treatment period and comprises therapeutically effective amounts of AT, PALP, TF and AGP or their active derivatives thereof.

All the above AT-containing compositions as well as the TF+PALP may also be used for the treatment of chronic wounds if inflammation is controlled by other means.

All the above compositions may also be used to treat non-wounded skin to reduce skin cell death and stimulate skin cell proliferation thereby preventing or restoring aging and other undesirable changes in the texture of skin.

Generally, the concentration of any of the active protein components in a composition for topical application will be at least about 0.01 wt.-%, and more suitably, between about 0.05 and about 1 wt.-%. In one embodiment, the composition comprises about 0.05 to about 0.5 wt.-% of each of the active component with a maximum total protein content of 1 wt.-%. In another embodiment, the composition contains between about 0.05 to about 0.5 wt.-% AT, between about 0.05 to about 0.5 wt.-% PALP, between about 0.05 to about 0.5 wt.-% TF, and between about 0.05 to about 0.5 wt.-% AGP with a maximum total protein content of 1 wt.-%.

The invention provides compositions for topical applications comprising either *vaselinum flavum* or *vaselinum album* or *vaselinum cholesteratum* and therapeutically effective amounts of at least two proteins as active components chosen from AT, PALP, TF and AGP. The composition may include one or more additives and/or enhancers that increase the effects of active protein components on skin cell proliferation and survival.

Topical Administration

The present invention provides methods for stimulating proliferation and reducing the death of skin cells, comprising the step of topically administering to an area of wounded or non-wounded area of the skin a composition comprising therapeutically effective amounts of at least two proteins as active protein components chosen from AT, PALP, TF and AGP or their active derivatives.

The methods described here are suitable for mammalian skin. The subject can be canine, porcine, horse, or bovine, for example. Most suitably, the subject is human.

In the practice of the methods, topical application of compositions is effective to stimulate proliferation and/or reduce the death of cells in the epidermis and dermis of the treated skin. Proliferation is stimulated when the rate of cell replication is increased, relative to the untreated condition, resulting in an increase in the number of skin cells. Increased cell survival also results in an increase in the number of skin cells because of decreased cell turnover. As demonstrated in the Examples, a visible sign of increased number of skin cells is related to a more cell-rich dermis and an increased number of epidermal layers. The methods of invention may also be effective to enhance or decrease, depending on the purpose, the influx of inflammatory cells (for example, leukocytes, macrophages) into the treated skin area.

The compositions may be applied to wounded (or damaged) or non-wounded areas of the skin. One definition for the term "wounded" as used herein refers to an area of skin that contains a wound such as a cut, puncture, abrasion, sore, scar, bruise, or burn of moderate- to high-degree. Such wounds can be caused by accidents, surgeries (including cosmetic surgeries), a serious health condition (for example, diabetes) or various cosmetic treatments. Another definition for "wounded" refers to a skin area where the skin lost its morphological continuity due to the physical loss of one or more skin layers, or to a skin area where the skin lost its function. Loss of function may not immediately or ever be associated with gross morphological changes such as loss of a skin layer. The term "non-wounded" refers to a skin area that has not lost physical continuity. Non-wounded skin can be healthy and non-healthy. Non-healthy skin partially lost its function. The purpose of applying a composition to healthy skin is to reduce or prevent deterioration of skin over time induced by various environmental stresses (such as excessive sunlight). The purpose of application of a composition to non-healthy, "non-wounded", skin (such as aging skin) is to reverse deterioration of skin's structure. The structure of "non-healthy, non-wounded" skin is inferior to that of healthy skin (for example, dermis and epidermis containing fewer cells and less collagen).

Topical administration can be accomplished via manual application of a composition such as a cream, a lotion, a gel and the like that includes the active components. A composition may be applied by other means, such as by spraying, applying with a pad or towel, etc. In some embodiments, a composition may be delivered by means of a dressing, bandage, patch, or other similar covering capable of releasing therapeutically effectively amounts of the active components. Other methods of delivering the active protein components are also within the scope of this invention.

The method may suitably be practiced using any of the compositions described above, comprising a physiologically compatible carrier and at least two of the active protein components or their active derivatives.

Regimens for Treating Wounds and Wound-Free Skin

The invention also provides regimens for restoring or maintaining the strength and thickness of damaged and undamaged skin, comprising periodically administering by topical application to the skin specific compositions containing effective amounts of at least two active protein components, chosen from AT, PALP, TF or AGP, or their active derivatives.

In the practice of the regimen, any of the compositions described above that contain at least two active protein components may be used as appropriate for a particular condition. For example, to avoid enhancing inflammation, a composition for treating chronic wounds does not contain AT; instead, the composition contains the anti-inflammatory AGP. Chronic wounds do not heal well partly because of the inhibitory effect of uncontrolled inflammation. In contrast, a composition for early treatment of non-chronic wounds may contain AT, instead of AGP, to promote inflammation that is initially required for starting the healing process. However, for later stage treatment of non-chronic wounds, AT is replaced with AGP to decrease inflammation, because chronic inflammation inhibits progression of the healing process. Likewise, for skin care products where the goal is to strengthen or at least maintain the strength of the skin, there may be no need to enhance inflammation by AT unless a specific circumstance arises that favors its inclusion into the composition.

In one method, the compositions are applied topically to the skin, as described above. The compositions are applied periodically over a period of time. As used with respect to the regimens described herein, the term "periodically" refers to repeated administration of the same or different compositions targeted to restoring or maintaining the strength and the thickness of the damaged and undamaged skin, over the time of treatment. The term "periodically" includes both repeated administration at fixed intervals and repeated administration over irregular intervals as is required by the subject's condition. The chosen composition(s) can be administered as needed. Alternatively, the chosen composition(s) can be administered two or more times a day. The frequency of administration of the composition(s) can vary and depend on the type of skin, the extent of injury, the location of the treated skin, the concentration of the active components in the composition, and the method used to administer the composition(s).

Generally, therapeutically effective amounts of the active components are administered. In the regimens of the invention, however, the effective amounts of the active components that are administered do not need to be identical for each separate administration. More or less of the active component may be administered in separate administrations, as the subject's needs dictate. A medical provider supervising treatment can adjust the administered dose to obtain the desired results.

The frequency of application and the duration of the regimen will depend on the size and nature (chronic, non-chronic) of the wound, the physiological state of the skin, the magnitude of response, and the level of satisfaction by the treated subject. In one embodiment of the regimen used for non-chronic wounds and/or transplanted skin, the same composition is applied once per day. In another embodiment of the regimen for non-chronic wounds and/or transplanted skin, which is a recommended treatment schedule, one composition is applied on the first and second day, while a second composition is applied several days later. This regimen may be repeated or the treatment may be continued exclusively with the second composition. In yet another embodiment of the regimen used for chronic wounds, the same composition may be applied every day, every second day, or every third day. A recommended treatment schedule for chronic wounds includes application of the same composition or sequentially two compositions every second day for the first week, twice-a-week for the second week, and once-a-week for the following weeks, for a time period that is determined by the level of success.

A recommended treatment schedule for wound-free unhealthy skin includes application of the same composition twice or thrice weekly for several months or for a time period as required to obtain the desired result. A recommended treatment schedule for wound-free healthy skin includes application of the same composition once or twice weekly. Variations to this treatment schedule will depend on the level of deterioration of skin and the level of success.

Administration by Injection

Also provided by the invention is a method for stimulating proliferation and reducing death of skin cells in mammalian skin, comprising a step of administering by injection a composition comprising a physiologically acceptable carrier, and therapeutically effective amounts of at least two active protein components chosen from AT, PALP, TF or AGP, or their active derivatives.

As a complement to the topical methods described above, other application methods, including various forms of injections, will also elicit the desired effects in the skin. In the case of injection, the active components will be transported to the skin either directly (such as for intradermal application or partly subcutaneous application) or via the blood supply (such as for intravenous, intraperitoneal, intramuscular or subcutaneous applications). A composition comprising at least two active components may be administered via intravenous injection, intraperitoneal injection, subcutaneous injection, intradermal injection, intramuscular injection, or any other mode of delivery that ensures appropriate distribution and relative stability of the proteins in the body.

For injection of a composition comprising at least two active protein components, the carrier may be any physiologically acceptable carrier that does not cause an undesirable physiological effect and is capable of ensuring proper distribution of the active components in the treated tissue. The active components are dissolved or dispersed in the physiologically acceptable carrier. Examples of carriers include physiological saline and phosphate-buffered saline. Alternatively, the active components may be enclosed in liposomes such as immunoliposomes, or other known delivery systems or formulations. The proteins may also be linked to specifically formulated nanoparticles suspended in a suitable liquid carrier. By way of example, each protein component can be readily dissolved in physiological saline (0.9 N NaCl), or in any other physiologically competent carrier, to yield a solution for injection.

An injectable composition may be prepared by dissolving or dispersing suitable preparations of the active protein components in the carrier using conventional methods. As examples only, one suitable composition for the practice in the method comprises at least two active protein components in a 0.9 N physiological salt solution to yield a total protein concentration of 10 mg/ml. Another suitable composition comprises at least two active protein components in a 0.9 N physiological salt solution to yield a total protein concentration of 200 mg/ml.

The injectable compositions may be modified by adding any number of additives and enhancers (as listed above for the topical application) that can be dissolved or suspended in the composition and that promote the effects of the active components or diminish any potential side effect.

In one embodiment of the method, the mode of injection is selected from intradermal, intravenous, subcutaneous, intramuscular, or intraperitoneal. The mode of injection is selected to provide either local delivery (such as intradermal application or partly subcutaneous application) or systemic delivery via the blood supply (such as intravenous, intraperitoneal and subcutaneous applications).

A common way to express a suitable dosage for systemic administration is grams of the active agent(s) per square meter of body surface area for the subject. Known formulas used for estimating a human subject's body surface area, based on the human's height (in cm) and mass (in kg) are suitable.

In case of intravenous, intramuscular, intraperitoneal, or subcutaneous application, a subject may be administered a total of about 0.1 to 5 g active protein components/$m^2$ once daily. In another embodiment, a subject may be administered by intravenous, intramuscular, intraperitoneal, or subcutaneous application a total of about 0.1 to about 5.0 g active protein components/$m^2$ twice or three times weekly. Alternatively, a subject may be administered a total of about 0.1 to about 5.0 g active protein components/$m^2$ biweekly by intravenous, intramuscular, intraperitoneal, or subcutaneous application.

In yet another embodiment, a subject may be administered a total of about 0.1 to about 5 g/$m^2$ by intravenous, intramuscular, intraperitoneal, or subcutaneous application once daily for several days, with the treatment then continued with less frequent applications of smaller doses.

One treatment of non-wounded skin is by intradermal injection of the chosen composition. For one injection site, the subject may be administered a total of about 0.01 to 1 mg of active proteins or their derivatives. Intradermal delivery of the composition can be performed once daily, three times week, twice a week, once a week, or once biweekly.

In some embodiments, any of the above-listed topical treatment can be combined with intradermal or systemic applications of the same or different compositions, chosen from AT, PALP, TF, or AGP, if such combination is selected by a medical provider.

If the chosen composite solution is injected locally, such as when the mode of injection is intradermal, aliquots of about 10 to 100 μL per injection site may be administered The concentration of the active components in the injectable composition combined may be in the range of about 1 to 30 mg/mL. Alternatively, the concentration of the active components combined may be in the range of about 2 to about 10 mg/mL. In one embodiment, several injection sites are used for one administration.

Intradermal application may be an especially effective and economical mode of application of the present compositions. Intradermal application may require use of less of the active protein components, as compared to other modes of injection. Also, for localized application the active components may be more effectively delivered or transported to the epidermal and dermal layers of the treated skin.

The invention further includes the use of AT, PALP, TF or AGP or their active derivatives in the manufacture of injectable compositions effective to stimulate proliferation and reduce the death of skin cells in wounded and non-wounded mammalian skin.

A specific method for delivery of proteins is via incorporating protein-containing implants such as, for example, small permeable capsules or permeable vials under the skin near to the damaged area. By selecting the content and pore size of the implants, it is possible to regulate the rate of outward diffusion of proteins.

Application of Protein Compositions to Transplanted Skin

The invention further provides a method for simultaneously stimulating proliferation and reducing death of skin cells in transplanted skin, as well as wounded host skin, comprising the step of topically administering to areas of the transplanted and wounded host skin a composition comprising therapeutically effective amounts of at least two active protein components, selected from AT, PALP, TF or AGP, or their active derivatives. Any of the above-specified topical compositions are suitable in the practice of this method. The method may be effective to enhance survival and proper functioning of the transplanted skin as well as promote the growth of the host skin (i.e. to increase the likelihood of a successful transplant).

In one embodiment of the method, the transplanted skin is human skin. In another embodiment of the method, the transplanted skin has been transplanted onto a human host. Another embodiment of the method includes a step of topically administering the composition to an area of host skin that is adjacent to the transplanted skin. In yet another embodiment, the chosen composition is administered to an area of host skin that is adjacent to the transplanted skin as well as the area of the transplanted skin. More than one composition, used sequentially or in a given order determined by a medical provider may be used for treating the same transplant.

The invention further includes the use of AT, PALP, TF, or AGP in the manufacture of suitable topical compositions effective to stimulate proliferation and reduce death of skin cells in the transplanted and wounded host skin.

The invention also provides a method for stimulating proliferation and reducing death of skin cells in the transplanted and wounded host skin, comprising the step of administering to areas of the transplanted skin and wounded host skin by injection a chosen composition comprising a physiologically acceptable carrier and therapeutically effective amounts of at least two active protein components, chosen from AT, PALP, TF, or AGP, or their active derivatives, dissolved or dispersed in the carrier. The method may be effective to enhance survival and proper functioning of the transplanted skin as well as promote the growth of the host skin (i.e. to increase the likelihood of a successful transplant). In one embodiment, the mode of injection is intradermal.

In some embodiments, any of the above-listed topical treatment of the transplanted and wounded host skin can be combined with intradermal or systemic applications of the same or different compositions, chosen from AT, PALP, TF, and AGP, or their active derivatives.

The invention further includes the use of AT, PALP, TF, and AGP, or their active active derivatives, in the manufacture of suitable injectable compositions effective to stimulate proliferation and reduce death of skin cells in the transplanted and damaged host skin.

In one embodiment, the transplant is a suspension of skin cells, such as, for example, human keratinocytes. The invention provides for the inclusion of various compositions, chosen from AT, PALP, TF, and AGP, or their active derivatives, in the skin cell suspension prior to transplantation. The proteins are suspended in the same carriers used for the skin cell suspensions. The proteins may be added to the skin cell suspension at any time prior to the transplantation procedure. Following incorporation and stabilization of transplanted skin cells in the host skin, additional treatment of the transplanted area with the above protein composition, dispersed in a suitable carrier, may be suitable. For the amount of proteins, the selection of protein components, and the frequency of treatments the same guidelines described for the treatment of wounded skin are applicable.

This invention may take on various modifications and alterations without departing from the spirit and scope thereof. Accordingly, it is to be understood that this invention is not to be limited to the above-described disclosures, but it is to be controlled by the limitations set forth in the following claims and any equivalents thereof. It is also to be understood that this invention may be suitably practiced in the absence of any element not specifically disclosed herein.

In describing preferred embodiments of the invention, specific terminology is used for the sake of clarity. The invention, however, is not intended to be limited to the specific terms so selected, and it is to be understood that each term so selected includes all technical equivalents that operate similarly.

EXAMPLES

Example 1

Purification and Spectrophotometric Assay of PALP

Human PALP (Type XXIV, 1020 units of total activity) in a partially purified form was obtained commercially from Sigma-Aldrich. A butanol extraction of placental tissue, followed by one or more chromatographic steps, was performed by Sigma-Aldrich to obtain the partially purified material. Butanol extraction inactivates most of the other placental proteins, including growth factors, but does not reduce the mitogenic or enzymatic activity of PALP.

As determined by sodium dodecyl sulfate-polyacrylamide gel electrophoresis (SDS-PAGE), the partially purified PALP obtained from Sigma-Aldrich (denoted "commercial PALP" herein) was not homogeneous and contained other proteins. FIG. 1 is an image of a gel separation of a preparation comprising commercial PALP without further purification, and other preparations of PALP of increasing purity. Separation of proteins was performed by conventional SDS-PAGE, and proteins were stained with coomassie blue stain. Lane 1 contains various molecular mass standards for comparison. Lane 2 represents a preparation containing commercial PALP with a strong 52 kDa band representing AT and another strong 66 kDa band representing a mixture of PALP and albumin. Lanes 3 and 4 represent preparations comprising commercial PALP material after further purification steps (described below), and lane 5 represents a preparation of homogeneous PALP obtained by the complete purification procedure described below.

A purification procedure consisting of several steps was performed to further purify the commercially obtained PALP to homogeneity. A similar purification procedure that is described elsewhere [She, Q.-B., Mukherjee, J. J., Huang, J.-S., Crilly, K. S. and Kiss, Z. (2000) *Growth factor-like effects of placental alkaline phosphatase in human and mouse embryo fibroblasts.* FEBS Lett. 469, 163-167] was followed, except that the last step was repeated.

A solution of commercial PALP was prepared by dissolving 350 mg of commercial PALP into 10 ml of buffer A (0.1 M sodium acetate, 0.5 M NaCl, 1 mM $MgCl_2$, 1 mM $CaCl_2$, adjusted to pH 6.5). This solution was then further purified by successive Concanavalin A-Sepharose and Q-Sepharose chromatography, essentially following the procedure described elsewhere [Chang, T.-C., Huang, S.-M., Huang, T.-M. and Chang, G.-G. (1992) *Human placenta alkaline phosphatase: An improved purification procedure and kinetic studies*. Eur. J. Biochem. 209, 241-247].

The solution was run through a Concanavalin A-Sepharose column followed by an elution step using buffer A as solvent. For elution, buffer A included 50 mM α-methyl-D-mannopyranoside. The active fractions collected from the effluent were pooled and dialyzed against buffer B (50 mM Tris-HCL at pH 7.7). SDS-PAGE separation of the collected and dialyzed fraction is shown in FIG. 1 in lane 3.

The collected and dialyzed fraction from the previous step was then passed through a Q-Sepharose column. The fraction of interest was eluted with buffer B using a linear gradient of 0-250 mM potassium phosphate at a pH of 7.5. The active fractions from the Q-Sepharose column were pooled and dialyzed against phosphate-buffered saline and concentrated by Amicon ultrafiltration. SDS-PAGE separation of the collected and dialyzed fraction is shown in FIG. 1 in lane 4, which demonstrates that at least two major proteins are still present in the fraction after dialysis.

Then, the collected and dialyzed fraction from the previous step was purified to homogeneity by t-butyl hydrophobic interaction chromatography (HIC) as described earlier [She, Q.-B., Mukherjee, J. J., Huang, J.-S., Crilly, K. S. and Kiss, Z. (2000) *Growth factor-like effects of placental alkaline phosphatase in human and mouse embryo fibroblasts*. FEBS Lett. 469, 163-167]. Prior to adding the fraction to the t-butyl HIC column, the fraction was made 2 M in ammonium sulfate, and pH was adjusted to 6.8. The 5 ml bed volume t-butyl HIC cartridge (BIO-RAD, Hercules, Calif.) was connected to a fast performance liquid chromatography (FPLC) system from PHARMACIA (Peapack, N.J.). The fraction was introduced to the HIC column, and the column was eluted with buffer C (100 mM sodium phosphate buffer, 2 M ammonium sulfate at pH 6.8). The column was eluted with buffer C until a first protein-containing fraction completely eluted, and then a negative gradient of 2 M-to-0 M ammonium sulfate in 100 mM sodium phosphate at pH 6.8 was passed over the column. The negative linear gradient was used to elute a second protein-containing fraction, which contained the enzymatically active PALP protein. The enzymatically active fraction from the HIC separation was dialyzed against phosphate buffered saline and concentrated by Amicon ultrafiltration. Presence and purity of the PALP enzyme in the fraction was confirmed by SDS-PAGE. After electrophorectic separation, the gel was stained using coomassie blue or silver stain for visual observation of protein bands. Often, a single protein band was observed with an approximate molecular weight of 66 kDa as shown in lane 5, FIG. 1. The pure PALP was further identified by sequence analysis performed by the Mayo Clinic Protein Core Facility (Rochester, Minn., USA) If the gel staining procedure still suggested the presence of a minor contaminant, (in about 40% of cases) the HIC chromatography step was repeated. Invariably, after the second HIC chromatography step, gel staining did not suggest the presence of any contaminant protein.

PALP enzyme activity was assayed using a spectroscopic method by monitoring the hydrolysis of 4-nitrophenylphosphate (as an increase in absorbance at 410 nm) at room temperature (22° C.) as described elsewhere [Chang, G.-G., Shiao, M.-S., Lee, K.-R. and Wu, J.-J. (1990) *Modification of human placental alkaline phosphatase by periodate-oxidized 1,$N^6$-ethenoadenosine monophosphate*. Biochem. J. 272, 683-690]. Activity analysis of 5-10 µg purified enzyme was performed in 1 mL incubation volume containing 50 mM $Na_2CO_3$/$NaHCO_3$, 10 mM $MgCl_2$, 10 mM 4-nitrophenylphosphate at pH 9.8. The extinction coefficient of 4-nitrophenol was taken as $1.62 \times 10^4$ $M^{-1}$ $cm^{-1}$. An enzyme activity of 1 U (unit) is defined as 1 µmol substrate hydrolyzed/min at 22° C. at pH 9.8.

Example 2

Purification of AT

A partially purified human placental alkaline phosphatase preparation (PALP) was acquired from Sigma-Aldrich, Inc. AT is a major contaminant of the commercially obtained PALP. AT was first further purified by successive Concanavalin A-Sepharose and Q-Sepharose chromatography as described by Chang et al. for the isolation of PALP [Chang, T.-C., Huang, S.-M., Huang, T.-M. and Chang, G.-G. (1992) *Human placenta alkaline phosphatase: An improved purification procedure and kinetic studies*. Eur. J. Biochem. 209, 241-247]. The Q-Sepharose fraction, which still contained placental alkaline phosphatase in addition to AT, was further purified to homogeneity by t-butyl HIC chromatography [She, Q.-B., Mukherjee, J. J., Crilly, K. S. and Kiss, Z. (2000) $\alpha_1$-*Antitrypsin can increase insulin-induced mitogenesis in various fibroblast and epithelial cell lines*. FEBS Lett. 473, 33-36]. The 5 ml bed volume t-butyl HIC cartridge was connected to a PHARMACIA FPLC system and the fractions containing AT were pooled. The purity was confirmed by SDS-PAGE (polyacrylamide gel electrophoresis) using coommassie blue stain. The purified protein was identified as AT by sequence analysis. The sequence analysis was performed independently by the Mayo Clinic Protein Core Facility (Rochester, Minn., USA). The protein concentration was determined by the Lowry assay, using bovine serum albumin as standard, with a protein assay kit from Sigma-Aldrich, Inc. according to the instructions. This purification procedure has been previously published [She, Q.-B., Mukherjee, J. J., Crilly, K. S. and Kiss, Z. (2000) $\beta_1$-*Antitrypsin can increase insulin-induced mitogenesis in various fibroblast and epithelial cell lines*. FEBS Lett. 473, 33-36].

Figure 2:
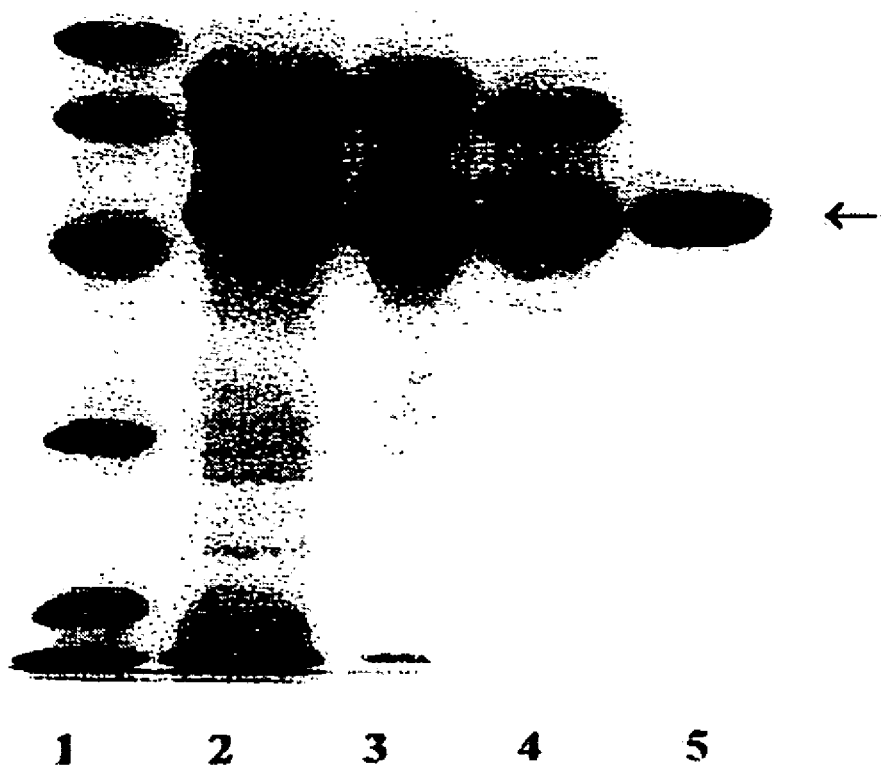
FIG. 2 is an image of gel separation, demonstrating that the AT used for the experiments shown in Tables 1 and 2 as well as FIGS. 3B, 5, 7, 10, 12, 14, 16, 17, 18 and 19 did not contain contaminating proteins at a detectable level.

FIG. 2 is an image of a stained gel. The gel includes the commercially obtained partially purified placental alkaline phosphatase preparation (shown in lane 2) further purified by successive Concanavalin A-Sepharose (lane 3), Q-Sepharose (lane 4), and t-butyl HIC chromatography using 2 M-to-0 M ammonium sulfate gradient (lane 5). Lane 1 contains molecular mass standards of 97 kDa (top), 66 kDa, 45 kDa, 31 kDa, and 22 kDa (bottom) in that order. FIG. 2 demonstrates that while the commercially obtained preparation contains three major proteins (one of them is AT as indicated by the arrow, while a ~66 kDa band represents placental alkaline phosphatase) and several minor proteins, the purified preparation contains only AT.

Examples 3-5

Combined Effects of AT, PALP, TF and AGP on Human Fibroblasts and Keratinocytes In Vitro Iron-free human Apo-TF (aTF) and iron-containing (iron content: 1100-1600 µg per 1-g protein) human holo-TF (hTF), both at least 97-98% pure, were purchased from Sigma-Aldrich (catalog numbers T 1147 and T 4132, respectively, according to the 2004/2005 Sigma Catalog). Essentially pure human AGP, isolated from human blood, was acquired from. Sigma-Aldrich (catalog number: G 9885 in 2004/2005 Sigma Catalog). Homogeneous PALP and AT were produced as described under Examples 1 and 2, respectively.

Recombinant wild-type PALP was produced according to the method described by Kozlenkov, et al. [Kozlenkov, A., Manes, T., Hoylaerts, M. F. and Millan, J. L. (2002) *Function assignments to conserved residues in mammalian alkaline phosphatases*. J. Biol. Chem. 277, 22992-22999]. To simplify the recovery and purification of recombinant PALP, the glycosylphosphatidylinositol anchoring sequence of PALP was replaced by the FLAG octapeptide, and the enzyme was expressed as secreted, epitope-tagged, protein.

Tissue culture reagents, including Dulbecco's Modified Eagle's Medium ("DMEM"), Minimum Eagle's medium ("MEM"), fetal calf serum ("FCS"), and fetal bovine serum ("FBS") were purchased from GIBCO-BRL (Rockville, Md.). (3-4,5-dimethylthiazol-2-yl)-2,5-diphenyltetrazolium bromide (MTT) was purchased from Sigma-Aldrich.

The human skin fibroblast cell line CCD 966 SK, derived from a 52-year-old subject, was purchased from American Type Culture Collection (Rockville, Md.). The fibroblasts, maintained in 10% FBS-containing MEM, were used between 4-7 passages before they started senesce. The immortalized human HaCaT keratinocyte cell line, isolated in 1988 [Boukamp, P., Petrussevska, R. T., Breitkreutz, D., Hornung, J. and Markham, A. (1988) *Normal keratinization in a spontaneously immortalized aneuploid human keratinocyte cell line*. J. Cell Biol. 106, 761-771], were maintained in 10% FCS-containing DMEM.

Examples 3-5 show the quantitative effects of AT, PALP, TF and AGP on fibroblast proliferation, and that of AT, PALP, and TF on keratinocyte proliferation, as determined by the MTT assay first described by Carmichael et al. [Carmichael, J., DeGraff, W. G., Gazdar, A. F., Minna, J. D. and Michell, J. B. (1987) *Evaluation of a tetrazolium-based semiatumated calorimetric assay: Assessment of chemosensitivity testing*. Cancer Res. 47, 936-942]. A fully automated version of this method was used in the experiments, as described below.

Fibroblasts were seeded at 1000 cells/well in 96-microwell plates in 10% FBS-containing MEM. HaCaT cells were seeded at 1000 cells/well in 96-microwell plates in 10% FCS-containing DMEM. After 24 hours, the medium was replaced with 80 µl of 2% FBS-containing fresh MEM medium (fibroblasts) or 2-10% FCS-containing DMEM (HaCaT cells) followed by treatments with individual proteins (10 µl each). At the end of the treatments the cultures were subconfluent (~65-85% confluent).

The relative changes in the number of viable cells were determined by the MTT assay. This photometric assay is based on the ability of healthy cells (mostly in the mitochondrial compartment) to reduce MTT to a blue formazan product. This technique is a widely used and accepted method to accurately determine the relative numbers of viable cells. For example, this is the official method used by the National Cancer Institute to screen anti-cancer drugs. In most cases, when the test agent does not strongly influence the oxidation-reduction balance of cells, the MTT assay is essentially a proliferation assay.

A MULTISKAN MS microplate reader, purchased from Labsystems (Franklin, Mass.), was used to measure the formation of formazan as an increase in absorbance at a test wavelength of 540 nm and a reference wavelength of 690 nm. In the data analysis, data were expressed as mean±standard deviation (S.D.) that the program calculated from 8 independent incubations performed in the same experiment. The key observations were reproducible in one or more follow-up experiments (for each treatment again using 8 independent incubations).

Example 3

Concentration-Dependent Effects of PALP, AT, TF, or AGP on the Proliferation of CCD 966 SK Fibroblasts Data for this Example is shown in Table 1. CCD 966 SK fibroblasts were separately treated for 72 hours, in the presence of 2% FBS, with increasing concentrations of homogeneous AT, homogeneous PALP (purified from placenta), commercial aTF, or commercial AGP. The measured extinction values ($A_{540}$), proportional with the number of viable cells, are listed. The concentration of proteins is given as µg/ml. The results indicate that PALP significantly, while AT and aTF moderately, enhance fibroblast proliferation; AGP is without effects. Approximate optimal concentrations for PALP, AT and aTF were 10-15, 100, and 10-15 µg/ml, respectively. The extinction value for fibroblasts at the beginning of treatment was 0.291±0.014.

TABLE 1

| Additions (µg/ml) | Viable fibroblasts ($A_{540}$) |
|---|---|
| None (Control) | 0.357 ± 0.021 |
| PALP, 2.5 | 0.404 ± 0.013 |
| PALP, 7.5 | 0.450 ± 0.018 |
| PALP, 15.0 | 0.477 ± 0.019 |
| PALP, 20.0 | 0.474 ± 0.027 |
| AT, 20.0 | 0.370 ± 0.027 |
| AT, 50.0 | 0.384 ± 0.014 |
| AT, 100.0 | 0.414 ± 0.022 |
| aTF, 2.5 | 0.411 ± 0.025 |
| aTF, 7.5 | 0.427 ± 0.017 |
| aTF, 15.0 | 0.440 ± 0.014 |
| aTF, 20.0 | 0.436 ± 0.018 |
| AGP, 20.0 | 0.340 ± 0.020 |
| AGP, 50.0 | 0.365 ± 0.017 |
| AGP, 100 | 0.346 ± 0.033 |

Example 4

Combined Effects of PALP, AT, TF, and AGP on Fibroblast Proliferation

Data for this Example is listed in Table 2. CCD 966 SK fibroblasts were treated for 72 hours, in the presence of 2% FBS, with homogeneous AT (100 µg/ml), recombinant PALP (10 µg/ml), commercial aTF or hTF (both at 15 µg/ml) and commercial AGP (100 µg/ml). The extinction values ($A_{540}$), proportional with the number of viable cells, are shown. The extinction value for fibroblasts at the beginning of treatment was 0.265±0.012. The results indicate that recombinant PALP also stimulates proliferation of fibroblasts; its effect was comparable with that of homogeneous PALP shown in the previous experiment (Table 1). AT moderately while both aTF and hTF significantly enhanced the effect of recombinant PALP. AT or AGP did not add to the combined effects of PALP and TF. This experiment demonstrates that both AT and particularly TF enhance the effects of PALP on skin cell proliferation in vitro.

TABLE 2

| Additions (μg/ml) | Viable fibroblasts (A$_{540}$) |
|---|---|
| None (Control) | 0.312 ± 0.018 |
| AT | 0.366 ± 0.022 |
| hTF | 0.393 ± 0.017 |
| aTF | 0.411 ± 0.020 |
| PALP | 0.427 ± 0.011 |
| AGP | 0.317 ± 0.015 |
| AT + PALP | 0.470 ± 0.021 |
| PALP + hTF | 0.507 ± 0.018 |
| PALP + aTF | 0.516 ± 0.023 |
| AT + PALP + hTF | 0.516 ± 0.017 |
| AT + PALP aTF | 0.527 ± 0.014 |
| AT + PALP + hTF + AGP | 0.522 ± 0.026 |
| AT + PALP + aTF + AGP | 0.535 ± 0.022 |

Example 5

Combined Effects of PALP, A T, TF, and AGP on the Proliferation of HaCaT Cells

Data for this Example is listed in Table 3. HaCaT keratinocytes were treated for 72 hours, in the presence of 2% or 10% FCS, with homogeneous AT (100 μg/ml), homogeneous PALP purified from placenta (10 μg/ml) and commercial aTF (15 μg/ml). The extinction values (A$_{540}$), proportional with the number of viable cells, are shown. The extinction value for HaCaT cells at the beginning of treatment was 0.367±0.020. The results indicate that PALP and aTF, particularly in combination, significantly enhance the proliferation rate of HaCaT cells. AT alone or in combination with PALP and aTF has little or no effects. This experiment demonstrates that PALP, particularly in combination with TF, enhances proliferation of keratinocytes in vitro.

TABLE 3

| Additions (μg/ml) | Viable fibroblasts (A$_{540}$) | |
|---|---|---|
| | 2% FCS | 10% FCS |
| None (Control) | 0.425 ± 0.017 | 0.498 ± 0.019 |
| PALP | 0.610 ± 0.022 | 0.576 ± 0.016 |
| AT | 0.463 ± 0.016 | 0.495 ± 0.025 |
| aTF | 0.522 ± 0.018 | 0.517 ± 0.022 |
| PALP + aTF | 0.672 ± 0.024 | 0.694 ± 0.027 |
| PALP + aTF + AT | 0.686 ± 0.029 | 0.708 ± 0.031 |

Examples 6-18

Effects of AT, PALP, TF, and AGP as well as their Combinations on the Epithelium and Dermis in Wounded and Non- Wounded Skin Examples 6-18 demonstrate that in mouse skin, or in human skin transplanted onto the back of mice, topical or intradermal application of combinations of AT, PALP, TF or AGP enhance the formation of epithelium in both wounded and non-wounded skin. The examples also demonstrate the ability of these combinations to prevent deterioration of the structure of dermis triggered by damaging effects such as solute injection or burning.

In all experiments, seriously compromised immune deficient ("SCID") mice were used. The mice were housed and handled under specific pathogen-free ("SPF") conditions. They were used at 8-14 weeks of age.

Most of the subsequent experimental procedures, outlined below, were described in detail by Juhasz et al. [Juhasz, I., Simon, Jr., M., Herlin, M. and Hunyadi, J. (1996) *Repopulation of Langerhans cells during wound healing in an experimental human skin/SCID mouse model*. Immunology Letters 52, 125-128]. The histological analysis by hematoxylin/eosin is a conventional procedure that has been described, for example, by Wankell et al. [Wankell, M., Munz, B., Hubner, G., Hans, W., Wolf, E., Goppelt, A. and Werner, S. (2001) *Impaired wound healing in transgenic mice overexpressing the activin antagonist follistatin in the epidermis*. The EMBO J. 20, 5361-5372]. An area of approximately 1.5 cm$^2$ on the dorsal skin of the subject mouse was shaved and treated with various creams composed of one or more active components selected from homogeneous placenta-derived AT, homogeneous placenta-derived PALP, commercial aTF or AGP mixed in *vaselinum cholesterinatum*. The following creams were prepared, in each case the indicated amount(s) of active component(s) being added to 1-g *vaselinum cholesterinatum*: (PALP cream) 1.2 mg PALP; (TF cream) 1.2 mg aTF; (AT/PALP cream) 1.2 mg AT+1.2 mg PALP; (PALP/TF cream) 1.2 mg PALP+1.2 mg aTF; (AT/TF cream) 1.2 mg AT+1.2 mg aTF; (AT/PALP/TF cream) 1.2 mg AT+1.2 m PALP+1.2 mg aTF; (PALP/TF/AGP cream) 1.2 mg PALP+1.2 mg aTF+1.2 mg AGP; and (AT/PALP/TF/AGP cream) 1.0 mg AT+1.0 mg PALP+1.0 mg aTF+1.0 mg AGP. An additional cream (control cream) consisted only of *vaselinum cholesterinatum*. For each application, 100-mg cream was massaged into 1-1.5 cm$^2$ shaved skin area. All samples for histological analysis were taken from the treated skin area.

In some experiments, the treated skin was human skin that had been grafted onto the mouse skin. Human foreskin preparations were donated by children at ages between 0.5-6 years. For the grafting procedure, a mouse (at age 6-8 weeks) was anesthetized with inhalation anesthetic methoxyflurane. SCID mice were utilized to minimize the risk of rejection of transplanted tissue by the host mouse. A circular graft bed of approximately 1.5 cm$^2$ was prepared on the lateral abdomen of the mouse by removing skin down to the fascia. The full-thickness donor foreskin was placed onto the wound bed and held in place with 5-0 monofilament sutures. The transplantation site was covered with a layer of non-stick gauze (CUTICERIN, available from Beiersdorf of Hamburg, Germany) and the adhesive bandage soaked with physiological saline and sutured to the dorsal and ventral skin of the animal with a surgical stitch. An additional layer of surgical tape was then applied. After 4-6 weeks of the surgery, the entire area of the transplanted skin was immersed into 65° C. water bath for exactly 12 seconds that caused second degree burns. The entire human skin area was treated with one of the creams within two minutes of completing the burning procedure. In each case, on the third day the bandage was removed and the treatment repeated. Samples were taken for the histology after six full days of treatments.

In some experiments, 50 μl of a composition containing 0.1 mg each of homogeneous placenta-derived AT, homogeneous placenta-derived PALP, and commercial aTF ("AT/PALP/TF composition") dissolved in 0.9 N NaCl was injected into either the mouse dorsal skin or the transplanted human skin. The control animals received the saline injection alone without the protein components.

For histology, skin samples were excised from the treated areas (for topical treatment) or within 1-3 mm distance from the site of injection (for treatment by intradermal injection). The excised skin samples were fixed in 4% paraformaldehyde in phosphate-buffered saline and embedded in paraffin so that several consecutive cross-sections could be made. Sections (6 μm) were stained with hematoxylin/eosin ("H&E"). At least 10-15 sections, derived from 3-5 animals were evaluated for the effectiveness of each type of treatment.

Images referenced in Examples 6-18 were selected to give the best representation of specific findings. However, it is important to note that, for example in case of burning, regeneration of skin does not take place evenly over the whole surface. New epithelium can be formed only from epithelial cells that survive burning, and these surviving cells are not evenly distributed. Accordingly, the extent of regeneration after 6 days of treatment will vary; in some areas, the epithelium will become several layers-thick, in some other areas it might only be one-cell layer thick upon treatments. In case of some treatments, particularly when performed with single agents, some areas of the treated skin may not have any epidermis.

Several images of burnt human skin, treated with the complete composition (AT/PALP/aTF/AGP), highlight such differences. This treatment, along with treatment with the AT/PALP/aTF and PALP/aTF/AGP creams, exerted the greatest effects on the formation of new epithelium. Comparison of the largest effects of various treatments on the thickness of epithelium (performed with an appropriate scale) revealed that treatment with the AT/PALP/aTF/AGP combination enhanced the thickness of epithelium about 2- and 3-times more than treatments with PALP/aTF and PALP alone, respectively, did.

Example 6

Figure 3:
FIG. 3A is a digital image of histological samples taken from the back of mice. Intradermal application of 0.9 M NaCl (physiological saline) caused dermal edema after 48 hours with no indication of new epidermis formation.
FIG. 3B is a digital image of histological samples taken from the back of mice. Intradermal application of a mixture of AT, PALP, TF and AGP in NaCl resulted in the influx of inflammatory cells into the dermis and in the formation of papillomatous surface (new epidermis) after 48 hours.
Figure 3:
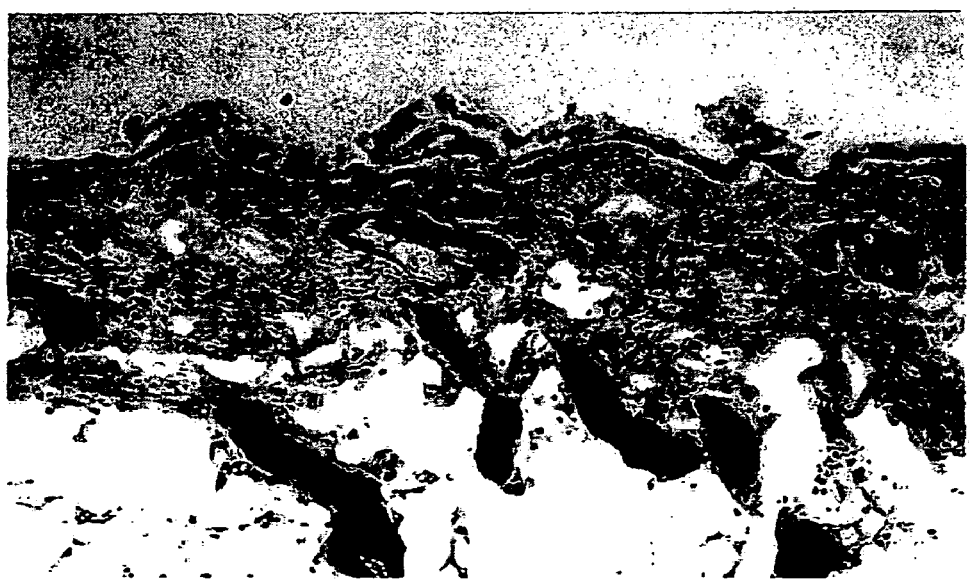

Effects of Intradermally Delivered A T/PALP/TF Composition on the Structure of Non-Wounded Mouse Skin An image of a representative histological sample from this. Example is shown in FIG. 3. In this experiment, either 50 μl of physiological saline alone (upper "A" panel) or 50 μl of a composition containing 0.1 mg each of homogeneous placenta-derived AT, homogeneous placenta-derived PALP, and commercial aTF ("AT/PALP/TF composition"), dissolved in 0.9 N NaCl, was injected into the dorsal areas of SCID mice (lower "B" panel). Tissue samples were taken for histochemistry 48 hours after the injections. Representative sections revealed that physiological saline alone caused edema, and this composition provided complete protection against this destructive process that was particularly evident in the dermis. In addition, the AT/PALP/TF composition (lower panel) clearly increased the formation of new epidermis (indicated by the blue color) as compared to the saline-treated control (upper panel).

Example 7

Figure 4:
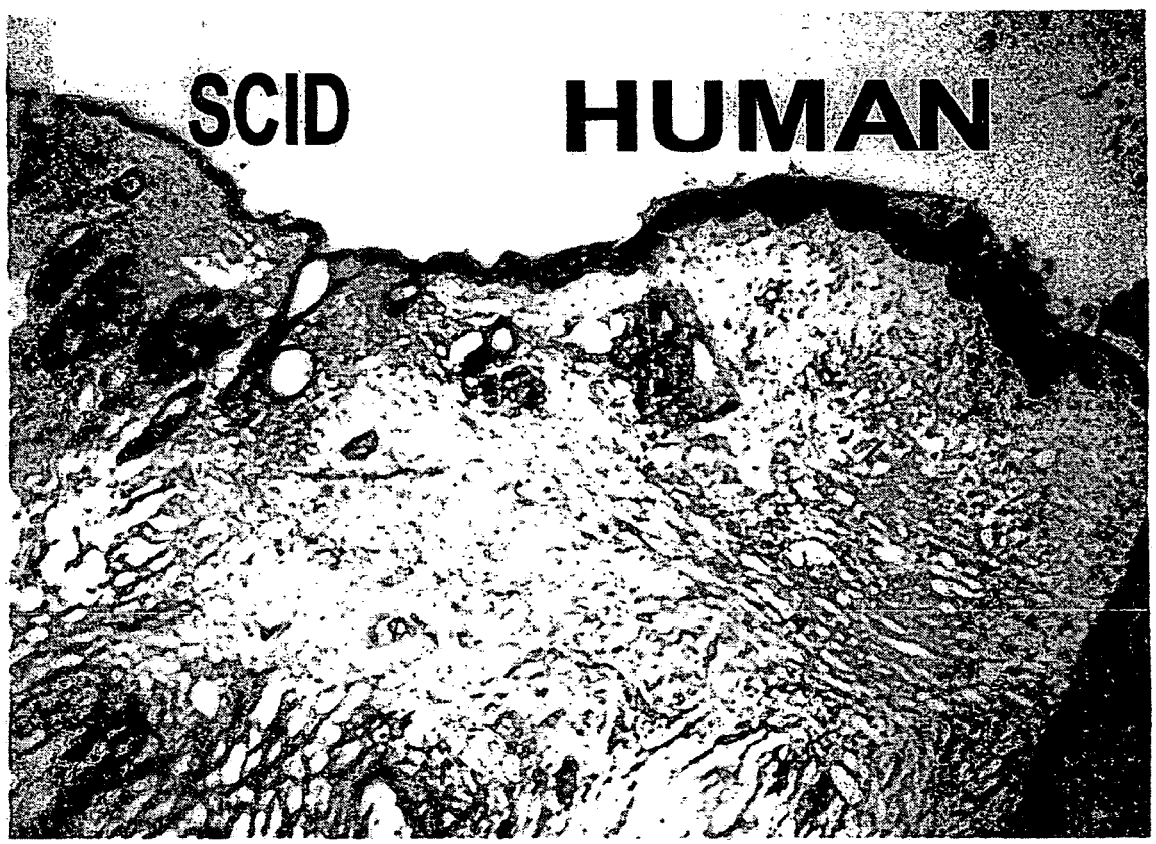
FIG. 4 is a digital image of a histological sample taken from the transplanted human skin (HUMAN), as shown on the right side, 48 hours after transdermal injection of physiological saline in the area of human skin. Also shown is a segment of mouse skin on the left side (SCID). The human skin contains several layers of epidermis, in contrast to the one-layer epidermis in the mouse skin. The epidermis of human skin did not significantly change upon injection of NaCl.
Figure 5:
FIG. 5 is a digital image of a histological sample taken from the transplanted human skin 48 hours after transdermal injection of a mixture of AT, PALP, TF and AGP in NaCl into the human skin area. The treatment resulted in significant thickening of the human epidermis in areas closer to the injection site, while in more remote areas no formation of new human epidermis was observed during that time period (shown on the far right side).

Effect of Intradermally Delivered AT/PALP/TF Composition on the Structure of Non-Wounded Human Skin In this experiment, either 50 μl of physiological saline alone (FIG. 4) or 50 μl of a composition containing 0.1 mg each of homogeneous placenta-derived AT, homogeneous placenta-derived PALP, and commercial aTF ("AT/PALP/TF composition"), dissolved in 0.9 N NaCl, was injected into the middle part of human skin (FIG. 5). Tissue samples were taken for histochemistry 48 hours after the injections. In FIG. 4, a representative section shows both the human skin with multiple layers of epidermis (right side, indicated as "HUMAN") and the mouse skin with a single layer of epidermis (left side, indicated as "SCID"). Injection of physiological saline alone caused some edema in the human skin and had no effect on the epidermis (FIG. 4). In human skin injected with the AT/PALP/TF composition there was no sign of edema in the dermis (FIG. 5). In addition to this protective effect, this composition enhanced the thickness of epidermis, a clear indication for increased mitotic activity of epidermal cells. This experiment indicated that the AT/PALP/TF composition is capable of enhancing proliferation of epidermal cells in human skin after intradermal application. Furthermore, this composition can protect the dermis against certain harmful effects.

Example 8

Figure 6:
FIG. 6 is a digital image of a histological skin sample taken from mouse back treated every second day for 20 days with *vaselinum cholesterinatum* alone. Such treatment did not change the one-layer structure of mouse epidermis.
Figure 7:
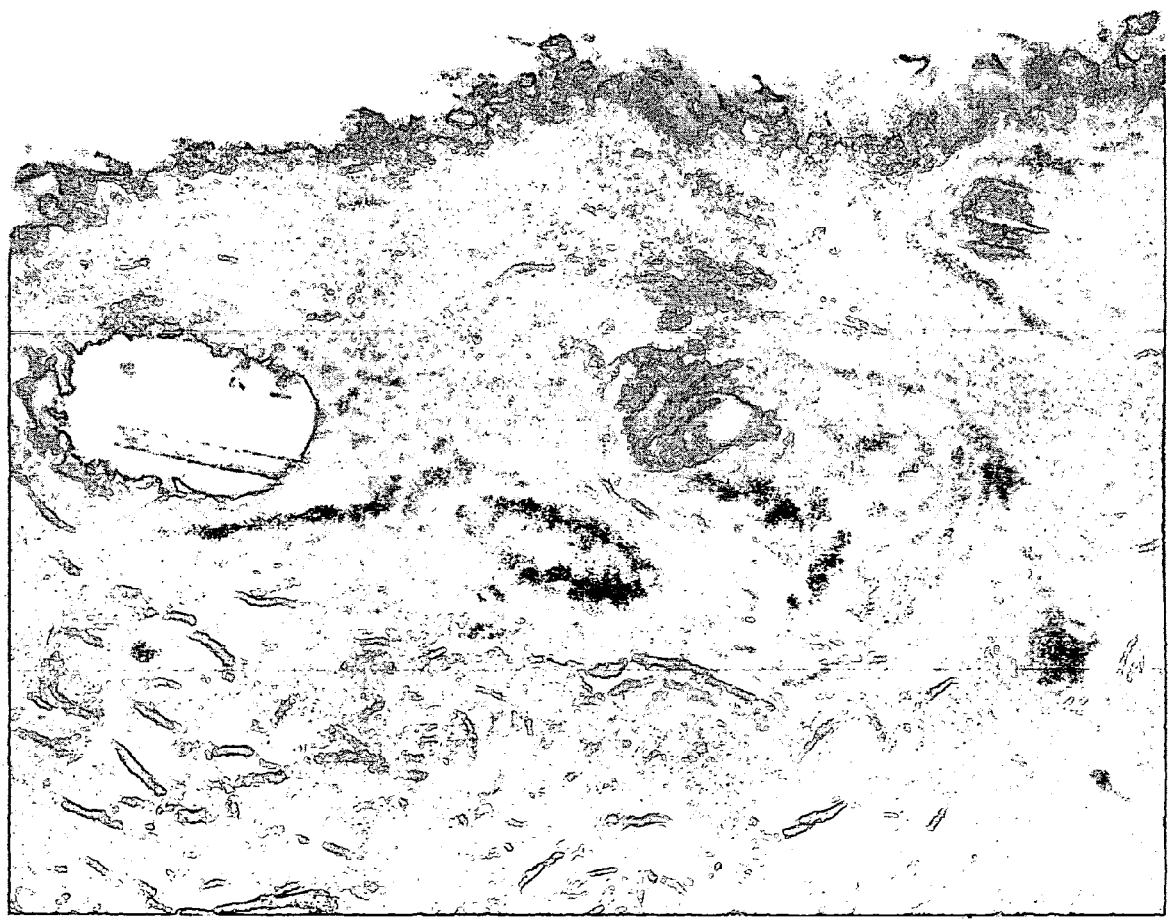
FIG. 7 is a digital image of a histological skin sample taken from mouse back treated every second day for 20 days with a mixture of AT, PALP, TF and AGP dispersed in *vaselinum cholesterinatum*. Such treatment added, on average, two new layers to the mouse epidermis and also increased the number of proliferating cells in the hair follicles as well as the number of inflammatory cells in the dermis.

Alterations in the Structure of Non-Wounded Mouse Skin Following Five Topical Treatments with the AT/PALP/TF Cream In this experiment, vaselinum cholesteratum (FIG. 6) or AT/PALP/TF cream (FIG. 7) was applied on the dorsal shaved skin on Days 1, 5, 9, 12, and 16, followed by sectioning and staining of tissue samples on day 20. The sections shown are representative of at least 15 sections. The representative image in FIG. 6 demonstrates that upon treatment with the vehicle cream, the epidermis remains thin consisting of only one layer of epidermal cells. The representative image in FIG. 7 demonstrates that prolonged, relatively infrequent, treatments of non-wounded skin with the AT/PALP/TF cream increase the number of epidermal layers from one to two-three. The treatments also led to an increase in the number of epidermal cells in and around the hair follicles (indicated by the intensity of blue color in the dermis that is stained red). This indicates that in case of mice the thin epidermis allows penetration of active components into the dermis. Furthermore, activation of epidermal cells in the hair follicles indicates that this composition should have a positive effect on hair growth.

Example 9

Alterations in the Structure of Non-Wounded Human Skin Following Five Topical Treatments with the AT/PALP/TF Cream In some experiments, vaselinum cholesteratum or AT/PALP/TF cream was applied on the transplanted non-wounded human skin on Days 1, 5, 9, 12, and 16, followed by sectioning and staining of tissue samples on day 20. The AT/PALP/TF cream clearly enhanced the formation of new epidermal cells. However, probably due to inefficient penetration through the upper layers of epidermis, the cream was significantly less effective in the human skin than in the mouse skin. This indicates that in case of topical application on intact human skin, the AT/PALP/TF cream may be more effective in enhancing formation of new epithelium in areas where the skin is thinner (for example, under the eye). Therefore, for most areas of intact human skin maximum effects may require intradermal application of the active protein-containing compositions.

Example 10

Figure 8:
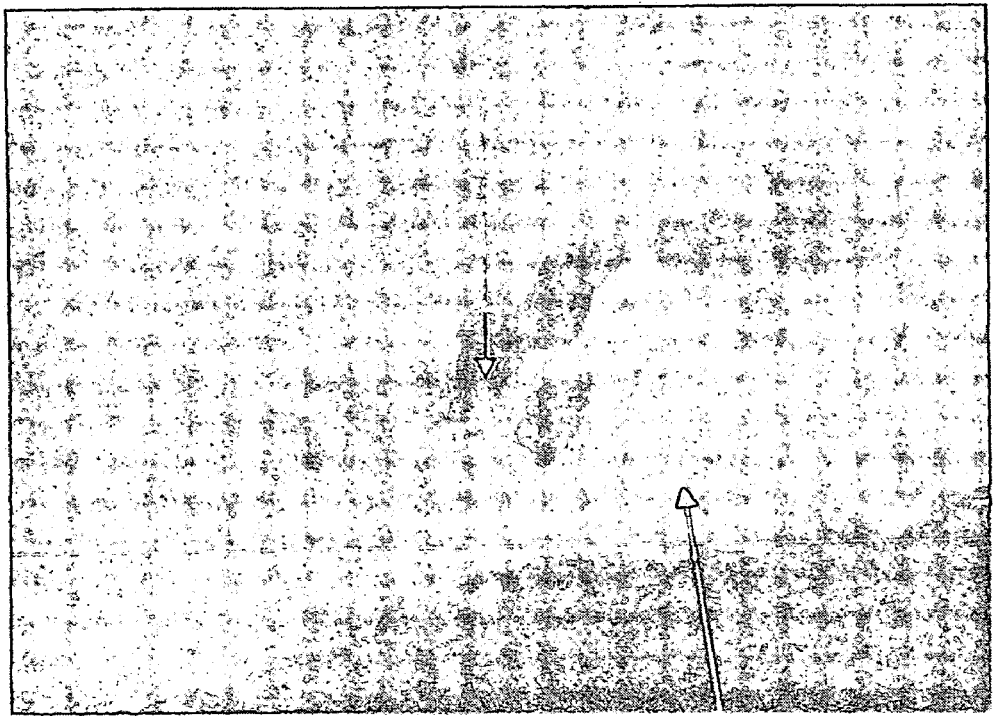
FIG. 8 is a digital image of a histological sample from transplanted human skin taken 6 days after immersing the skin into 65° C. water and treating twice with *vaselinum cholesterinatum* alone. There are no proliferating cells in the remaining, clearly less viable, epidermis. The white arrow points to epidermis, while the black arrow points to the acantholysis due to burn. The black start indicates dermis.
Figure 9:
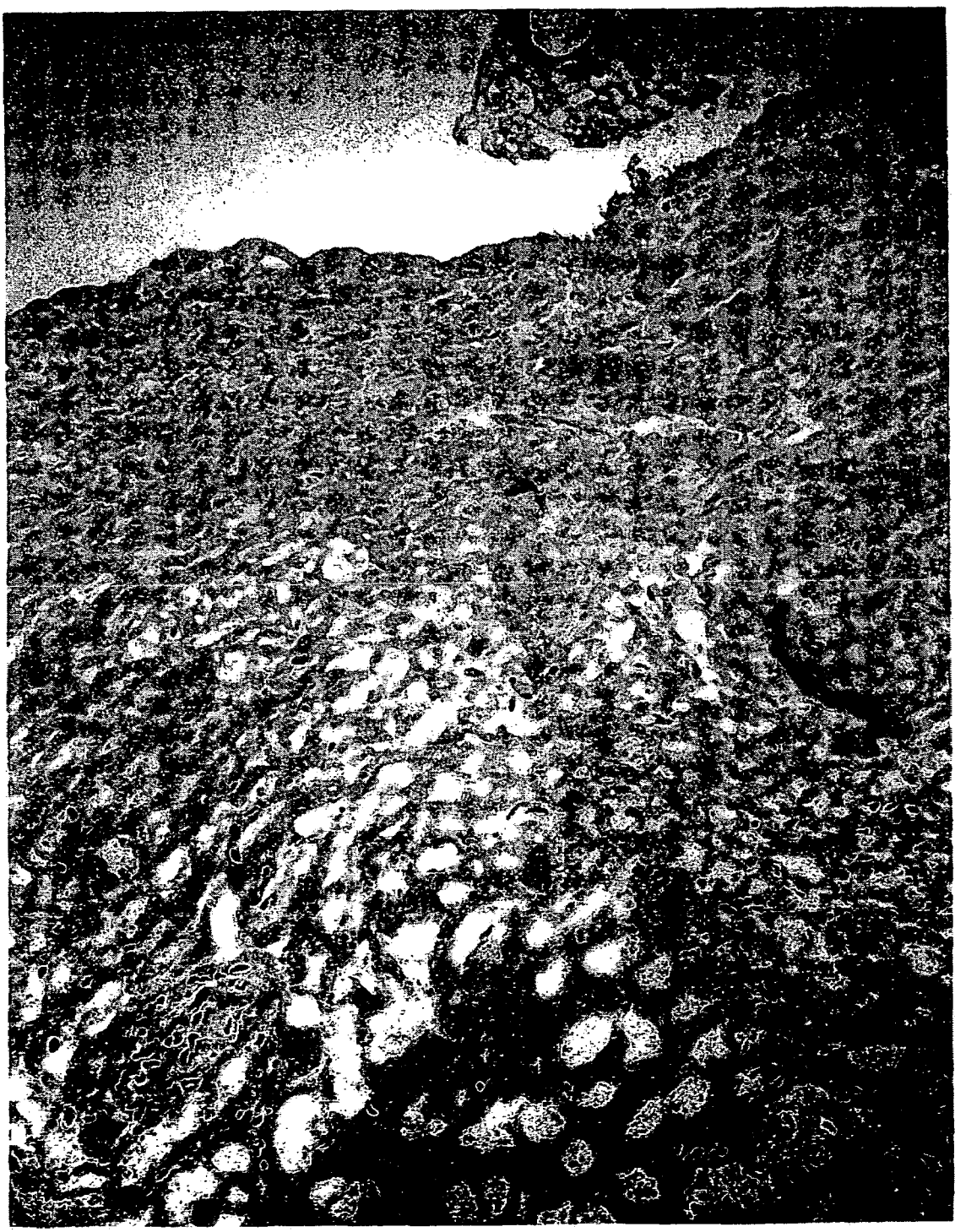
FIG. 9 is a digital image of a histological sample from transplanted human skin taken 6 days after immersing the skin into 65° C. water and treating twice with *vaselinum cholesterinatum* alone. There is no epidermis or any sign of new epidermis formation; the dermis shows considerable damage.
Figure 10:
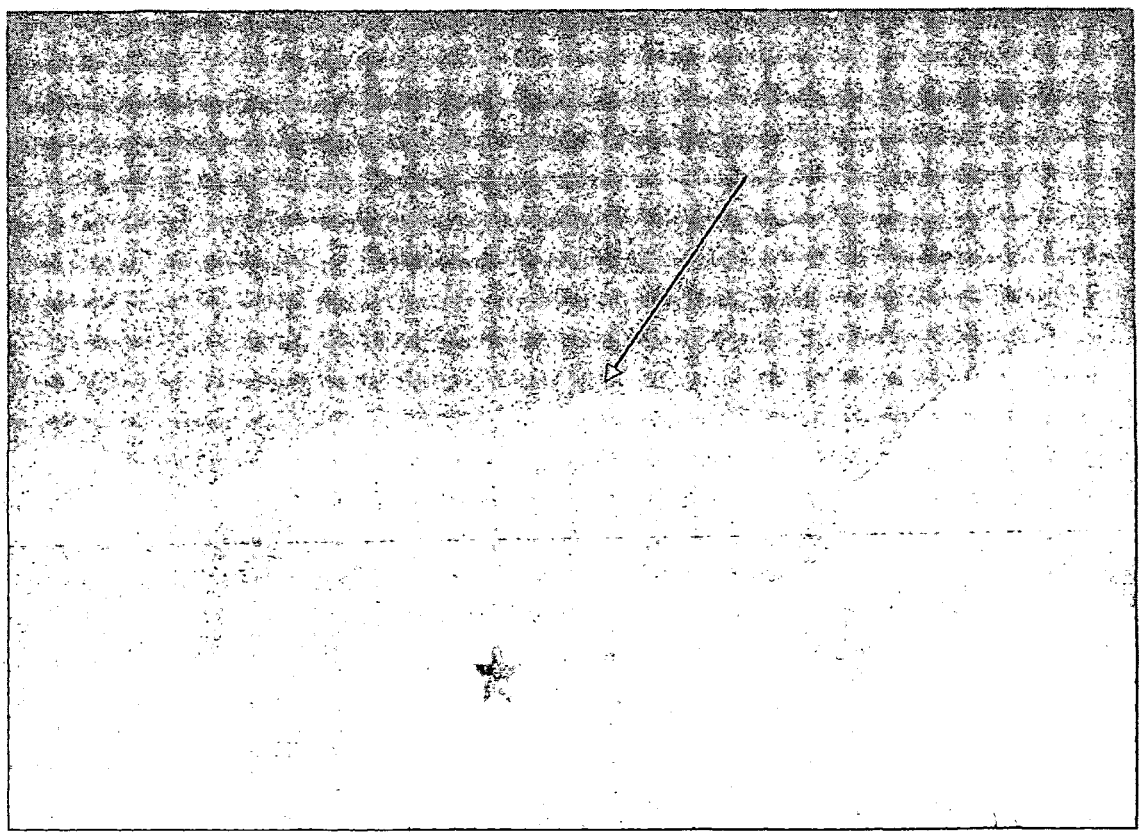
FIG. 10 is a digital image of a histological sample from transplanted human skin taken 6 days after immersing the skin into 65° C. water and treating twice with a mixture of AT, PALP, TF and AGP dispersed in *vaselinum cholesterinatum*. The arrow shows the column structure of re-forming epidermis above the dermis that is indicated by a star.

Effect of an AT/PALP/aTF/AGP Composition on the Structure of Burnt Human Skin The area of human skin transplanted onto the dorsal mouse skin was immersed into hot water (65° C.) for 12 sec. This was followed, within 2 minutes, by treatments with topical administration of either the vehicle *vaselinum cholesteratum* or a composition containing homogeneous placenta-derived AT (1.5 mg), homogeneous placenta-derived PALP (0.5 mg), commercial aTF (0.5 mg), and commercial AGP (1.5 mg) per 1-g of *vaselinum cholesteratum*. FIG. 8 demonstrates that 6 days after treating the burnt human skin with *vaselinum cholesteratum* alone did not help regeneration of the epidermis (which remains seriously damaged) which is separated from the also damaged, less cellular, dermis. FIG. 9 represents a different area of burn human skin treated with *vaselinum cholesteratum* alone for 6 days. This area has no epidermis at all, and the dermis is less cellular than in the normal skin (the white spots represent missing cells). In contrast, treatment of the burnt human skin with the AT/PALP/aTF/AGP preparation for 6 days resulted in the formation of new epidermis (seen as columns) as indicated by the black arrow in FIG. 10. Although this composition was effective in stimulating the formation of epidermis, to achieve even better results, in subsequent experiments the amount of PALP and aTF was increased at the expense of AT and AGP. In the following experiments, the effects of various compositions on the burnt human skin are to be compared to the effects of *vaselinum cholesteratum* alone as shown in FIG. 8 and FIG. 9.

Example 11

Effects of the PALP Cream on the Epidermis and Dermis of Burnt Human Skin

Figure 11:
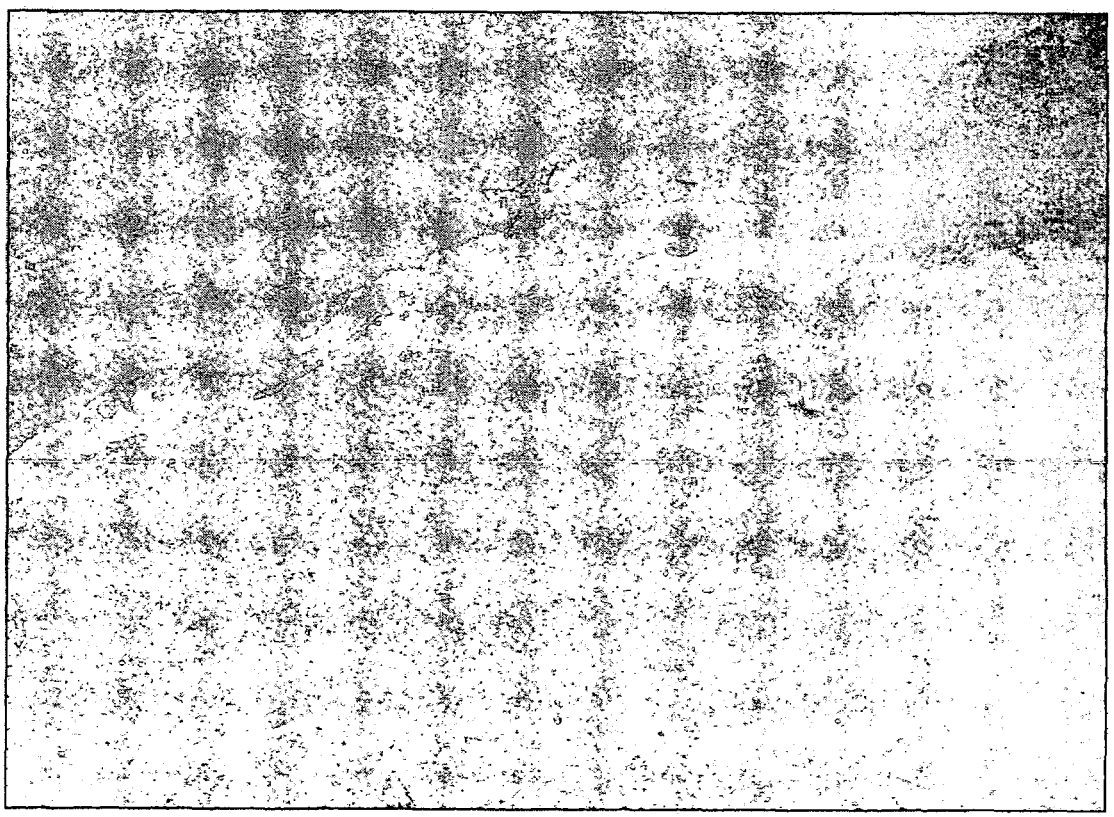
FIG. 11 is a digital image of a histological sample from transplanted human skin taken 6 days after immersing the skin into 65° C. water and treating twice with highly purified PALP dispersed in *vaselinum cholesterinatum*. PALP increased the influx of inflammatory cells into the upper region of dermis and it also induced the formation of new epidermis.

The area of human skin transplanted onto the dorsal mouse skin was immersed into hot water (65° C.) for 12 sec. This was followed, within 2 minutes, by treatments with topical administration of a cream containing homogeneous placenta-derived PALP (1.2 mg) in 1-g of *vaselinum cholesteratum*. The treatment was repeated on Day 3, and samples for histochemistry were taken on Day 6. FIG. 11 is a representative image indicating the presence of thin epidermis in the PALP-treated human skin. Also, in the PALP-treated skin (FIG. 11) the dermis clearly contains more cells than the dermis in the skin treated with *vaselinum cholesteratum* alone (FIGS. 8, 9).

Example 12

Figure 12:
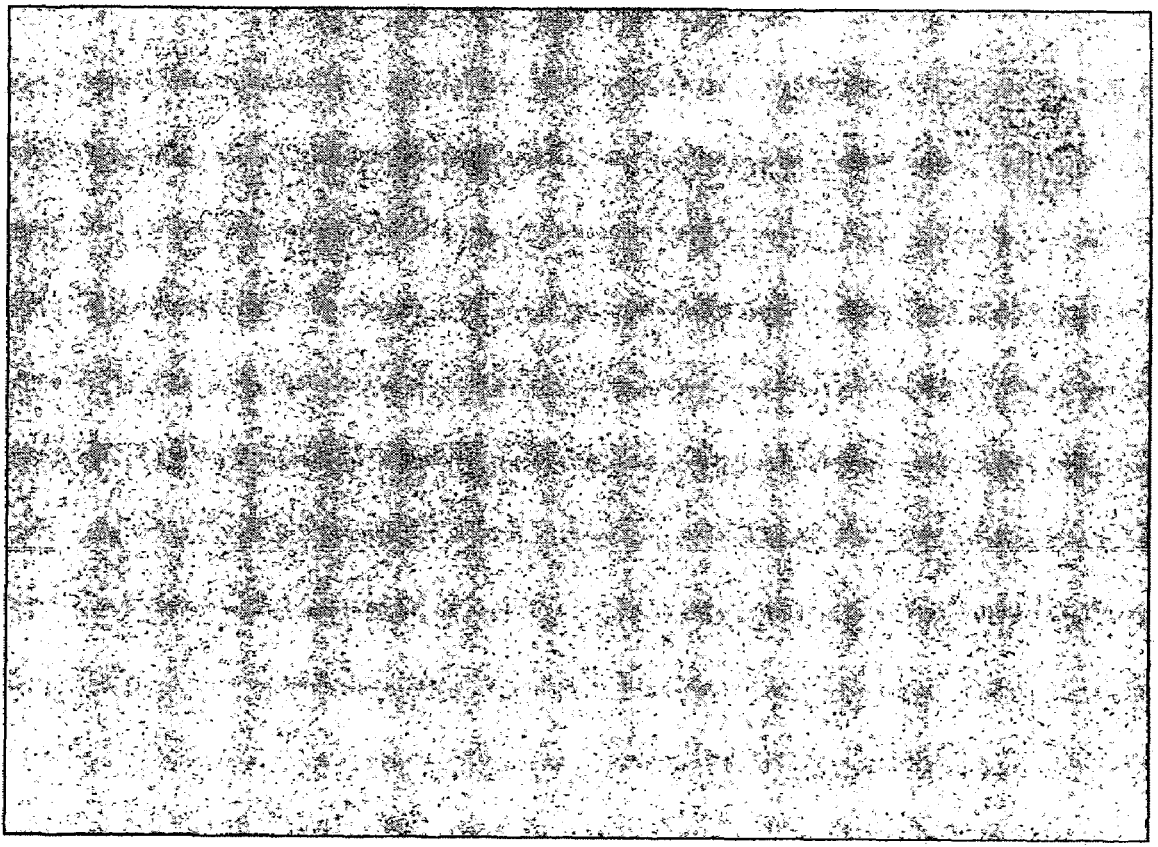
FIG. 12 is a digital image of a histological sample from transplanted human skin taken 6 days after immersing the skin into 65° C. water and treating twice with a mixture of highly purified PALP and AT dispersed in *vaselinum cholesterinatum*. The mixture of PALP+AT increased the influx of inflammatory cells into the upper region of dermis and induced the formation of new epidermis to a somewhat greater degree than PALP did alone.

Effects of the A T/PALP Cream on the Epidermis and Dermis of Burnt Human Skin The area of human skin transplanted onto the dorsal mouse skin was immersed into hot water (65° C.) for 12 sec. This was followed, within 2 minutes, by treatments with topical administration of a cream containing homogeneous placenta-derived AT (1.2 mg) and homogeneous placenta-derived PALP (1.2 mg) in l-g of *vaselinum cholesteratum*. The treatment was repeated on Day 3, and samples for histochemistry were taken on Day 6. FIG. 12 indicates the presence of epidermis that generally was slightly thicker than the epidermis in the skin treated with PALP alone. Again, the dermis in the AT/PALP-treated skin (FIG. 12) clearly contains more cells than the dermis in the skin treated with *vaselinum cholesteratum* alone (FIGS. 8, 9). Because of the relatively weak effects of AT on skin cell proliferation, a strong effect of AT alone on wound healing was not expected. Therefore, the effect of AT alone on wound healing was not examined. However, in the retrospective, the results suggest that AT even alone may have some detectable positive effects on wound healing, at least in case of the burnt skin.

Example 13

Effects of the aTF Cream on the Epidermis and Dermis of Burnt Human Skin

Figure 13:
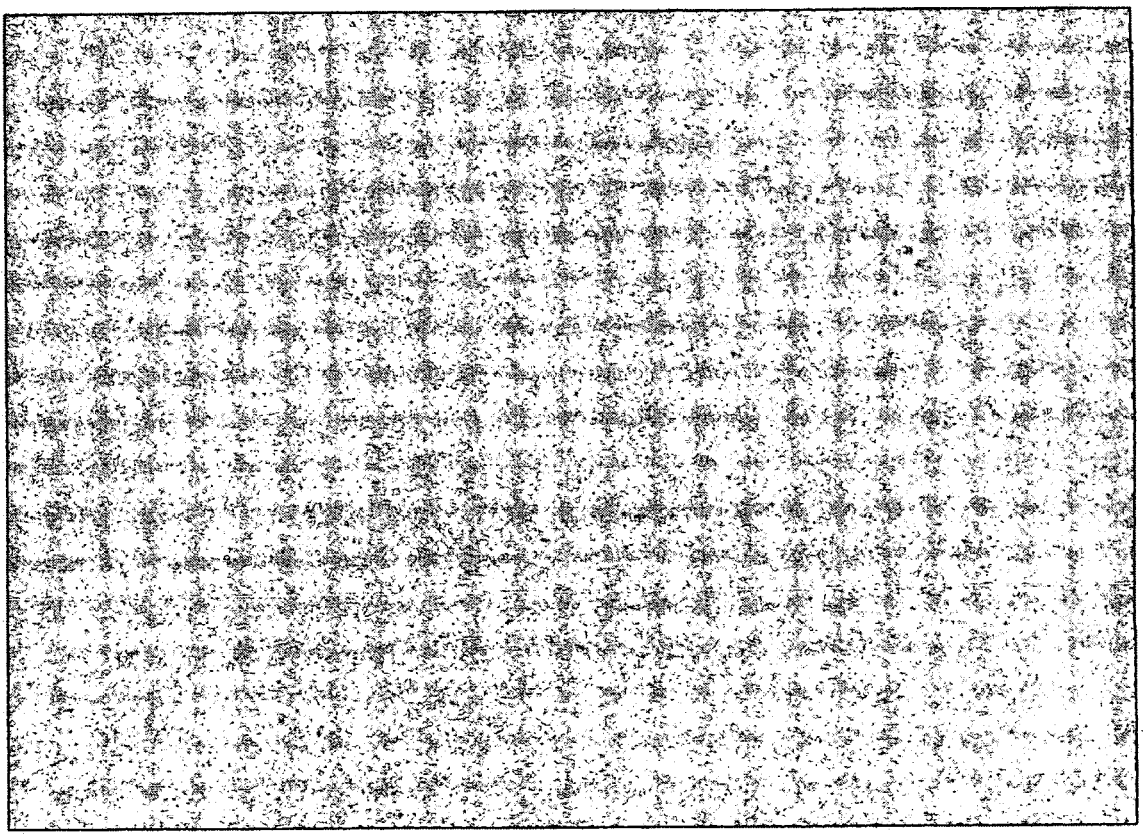

The area of human skin transplanted onto the dorsal mouse skin was immersed into hot water (65° C.) for 12 sec. This was followed, within 2 minutes, by treatments with topical administration of a cream containing commercial aTF (1.2 mg) in 1-g of *vaselinum cholesteratum*. The treatment was repeated on Day 3, and samples for histochemistry were taken on Day 6. FIG. 13 shows that aTF-treated human skin contains a thin epithelial layer comparable to that observed with the PALP cream (FIG. 11), while the structure of dermis shows more signs of damage in the aTF- than PALP-treated skin. Overall, the results indicated that aTF has positive effects on the structure of burnt skin.

Example 14

Figure 14:
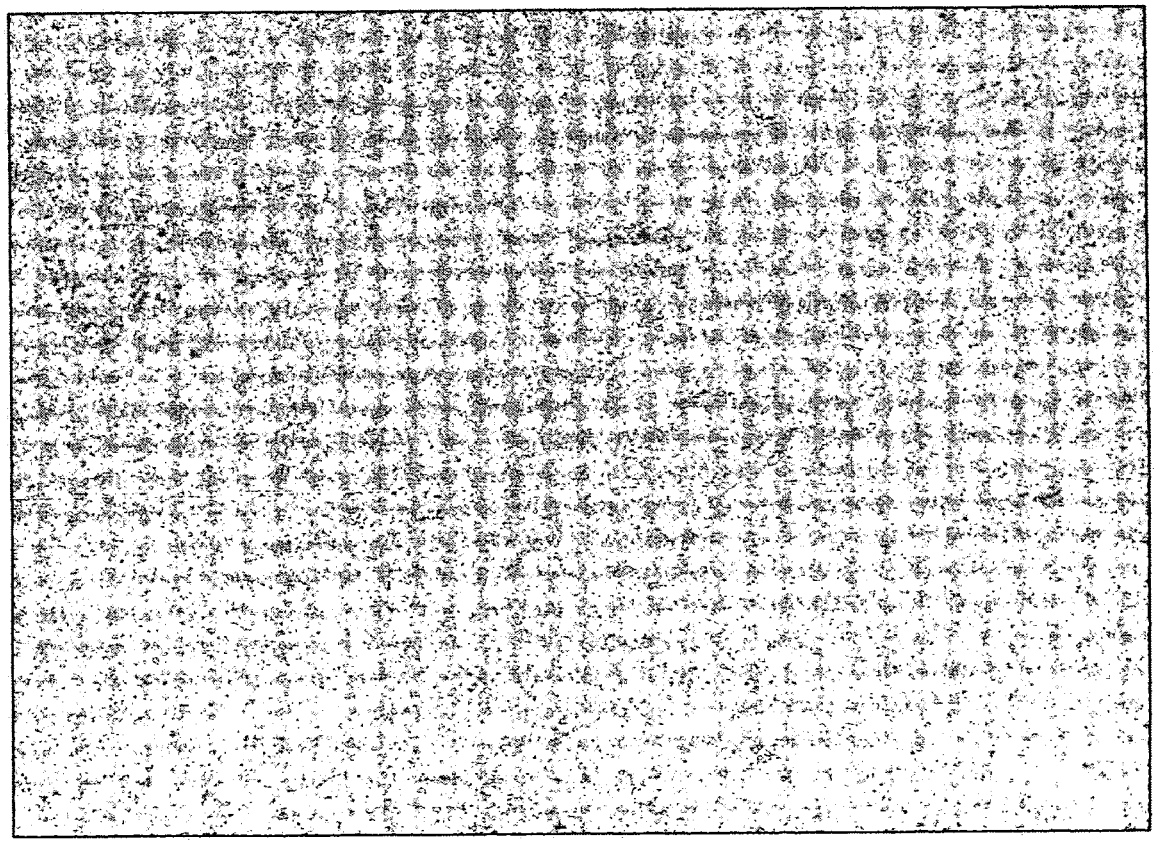
FIG. 14 is a digital image of a histological sample from transplanted human skin taken 6 days after immersing the skin into 65° C. water and treating twice with a mixture of aTF+AT dispersed in *vaselinum cholesterinatum*. The mixture aTF+AT increased the influx of inflammatory cells into the dermis and induced the formation of new epidermis; overall, this combination may be somewhat more effective than aTF alone.

Effects of the AT/aTF Cream on the Epidermis and Dermis of Burnt Human Skin The area of human skin transplanted onto the dorsal mouse skin was immersed into hot water (65° C.) for 12 sec. This was followed, within 2 minutes, by treatments with topical administration of a cream containing homogeneous placenta-derived AT (1.2 mg) and commercial aTF (1.2 mg) in 1 -g of *vaselinum cholesteratum*. The treatment was repeated on Day 3, and samples for histochemistry were taken on Day 6. FIG. 14 shows that treatment of burnt human skin with this cream resulted in the formation of epidermis that was comparable to that obtained with AT+PALP (FIG. 12). The treatment with AT/PALP also increased the cellular content of dermis just like the AT/PALP-containing cream did.

Example 15

Figure 15:
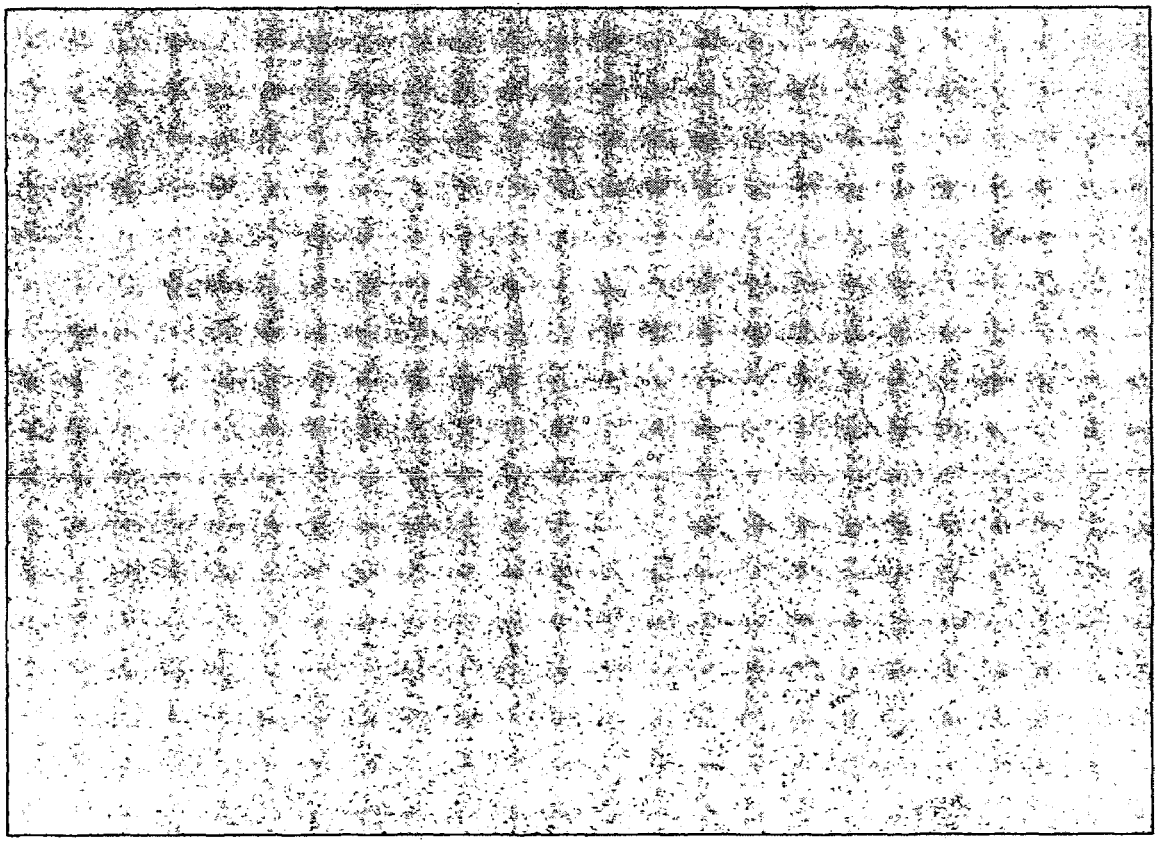
FIG. 15 is a digital image of a histological sample from transplanted human skin taken 6 days after immersing the skin into 65° C. water and treating twice with a mixture of PALP+aTF dispersed in *vaselinum cholesterinatum*. The mixture of PALP+aTF increased the influx of inflammatory cells into the dermis and promoted the formation of new epidermis somewhat more efficiently than PALP did alone.

Effects of the PALP/aTF Cream on the Epidermis and Dermis of Burnt Human Skin The area of human skin transplanted onto the dorsal mouse skin was immersed into hot water (65° C.) for 12 sec. This was followed, within 2 minutes, by treatments with topical administration of a cream containing homogeneous placenta-derived PALP (1.2 mg) and commercial aTF (1.2 mg) in 1-g of *vaselinum cholesteratum*. The treatment was repeated on Day 3, and samples for histochemistry were taken on Day 6. FIG. 15 shows the presence of several layers of epidermis and a strongly cellular dermis in the PALP/aTF-treated human skin. Overall the combined effects of PALP+aTF (FIG. 15) on the formation of epidermis and preservation of dermis were greater than the effects of PALP alone (FIG. 11).

Example 16

Figure 16:
FIG. 16 is a digital image of a histological sample from transplanted human skin taken 6 days after immersing the skin into 65° C. water and treating twice with a mixture of AT+PALP+TF dispersed in *vaselinum cholesterinatum*. Overall, the mixture of AT+PALP+aTF increased the formation of new epidermis to greater extents than any of the two-protein combinations did. Note that increase in epidermis thickness is somewhat uneven, which is characteristic of regenerating skin.

Effects of the AT/PALP/aTF Cream on the Epidermis and Dermis of Burnt Human Skin The area of human skin transplanted onto the dorsal mouse skin was immersed into hot water (65° C.) for 12 sec. This was followed, within 2 minutes, by treatments with topical administration of a cream containing homogeneous placenta-derived AT (1.2 mg), homogeneous placenta-derived PALP (1.2 mg), and commercial aTF (1.2 mg) in 1-g of *vaselinum cholesteratum*. The treatment was repeated on Day 3, and samples for histochemistry were taken on Day 6. FIG. 16 shows the formation of thick epidermis in patches separated by less developed regions of epidermis. Overall, this treatment was more effective to restore epidermis in burnt human skin than treatments with PALP alone or with the PALP/aTF, AT/PALP, and AT/aTF combinations. Thus, the AT/PALP/aTF combination can be recommended for the immediate treatment of non-chronic wounds.

Example 17

Effects of the AT/PALP/aTF/AGP Cream on the Structure of Burnt Human Skin

Figure 17:
FIG. 17 is a digital image of a representative histological sample from transplanted human skin taken 6 days after immersing the skin into 65° C. water and treating twice with a mixture of AT+PALP+aTF+AGP dispersed in *vaselinum cholesterinatum*. Overall, AT+PALP+aTF+AGP appeared to have slightly greater effects than the AT+PALP+aTF combination on the formation of new epidermis. However, note that the thickness of epidermis is again uneven.
Figure 18:
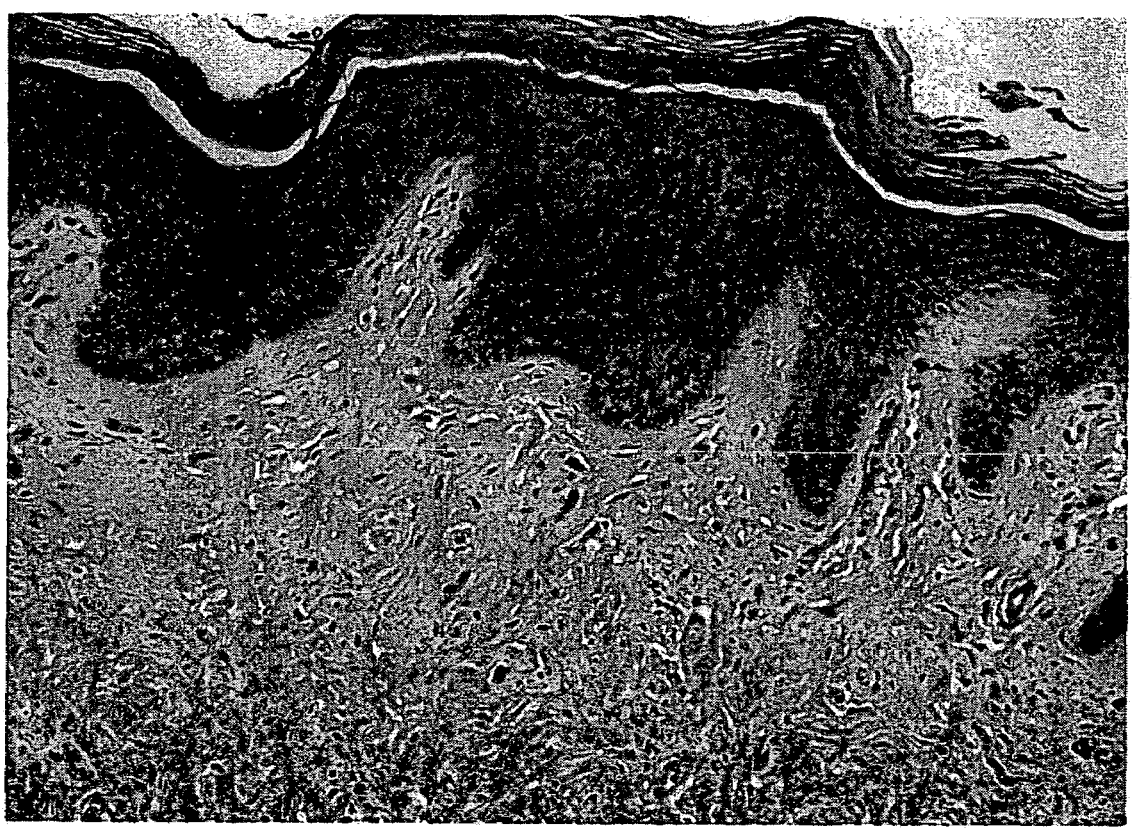
FIG. 18 is a digital image of another representative histological sample from transplanted human skin taken 6 days after immersing the skin into 65° C. water and treating twice with a mixture of AT+PALP+aTF+AGP dispersed in *vaselinum cholesterinatum*. This provides additional example that this combination is a powerful promoter of epidermis formation.
Figure 19:
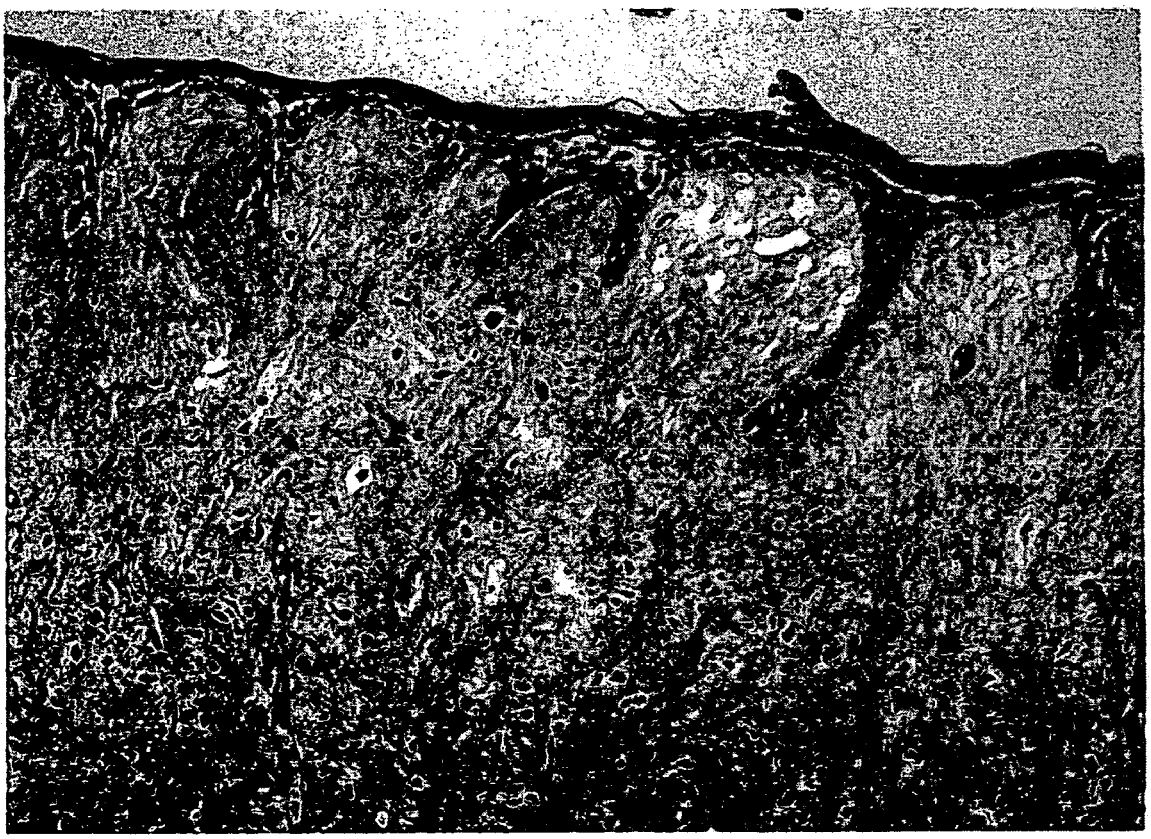
FIG. 19 is a digital image of a yet another representative histological sample from transplanted human skin taken 6 days after immersing the skin into 65° C. water and treating twice with a mixture of AT+PALP+aTF+AGP dispersed in *vaselinum cholesterinatum*. In this skin area newly formed epidermis takes up the characteristic finger-like shapes. This often observed phenomenon most probably reflects that new epidermis formation starts out from surviving islets of epithelial cells in the basal layer and that newly formed cells first move upward before moving sideways.

The area of human skin transplanted onto the dorsal mouse skin was immersed into hot water (65° C.) for 12 sec. This was followed, within 2 minutes, by treatments with topical administration of a cream containing homogeneous placenta-derived AT (1.2 mg), homogeneous placenta-derived PALP (1.2 mg), commercial highly purified aTF (1.2 mg), and commercial highly purified AGP in 1-g of *vaselinum cholesteratum*. The treatment was repeated on Day 3, and samples for histochemistry were taken on Day 6. As it is true for each previous treatment, while topical application of this composition generally enhanced the thickness of epidermis, the shape and thickness of epidermis showed large variations depending on the area from which the sample was taken. For example, FIG. 17 shows a large area of treated human skin where the epidermis became several layers-thick, although on the far left side of the picture the epidermis is thinner. FIG. 18 is another representative image showing alternation in the developing epidermis of thicker and thinner regions. The most likely explanation for this phenomenon is that new epithelial cells are derived from surviving patches of the lower "basal" layer, where the mitotically active epithelial cells reside. Newly formed cells then first move upward and then sideways creating a new epidermis with uneven thickness after 6 days of treatment. As yet another representative observation, FIG. 19 shows an image of a larger area of treated human skin taken at lower magnification. The characteristic finger-like epidermal structures seen in the picture can again be explained by assuming that formation of new epithelium starts from patches of mitotic epidermal cells in the lower basal layer which then move upward. The differences between the areas shown in FIGS. 17 and 19 may be that in the former case (FIG. 17) formation of new epidermis is at a more advanced stage (indicated by more even thickness of epidermis) than in the latter case (FIG. 19). It should be noted that the fingerlike structure of epidermis is not unique for the above treatments; newly formed epidermis generally shows such fingerlike structure.

Example 18

Figure 20:
FIG. 20 is a digital image of a representative histological sample from transplanted human skin taken 6 days after immersing the skin into 65° C. water and treating twice with a mixture of PALP+aTF+AGP dispersed in *vaselinum cholesterinatum*. Overall, PALP+aTF+AGP appeared to have slightly greater effects than the PALP+aTF combination, and somewhat smaller effects than the 4-protein combination, on the formation of new epidermis. However, note that the thickness of epidermis is uneven which allows only semi-quantitative evaluation of the differences in the effects of different compositions.

Effects of the PALP/aTF/AGP Cream on the Epidermis and Dermis of Burnt Human Skin The area of human skin transplanted onto the dorsal mouse skin was immersed into hot water (65° C.) for 12 sec. This was followed, within 2 minutes, by treatments with topical administration of a cream containing homogeneous placenta-derived PALP (1.2 mg), commercial aTF (1.2 mg), and commercial AGP (1.2 mg) in 1-g of *vaselinum cholesteratum*. The treatment was repeated on Day 3, and samples for histochemistry were taken on Day 6. FIG. 20 shows that in some areas of human skin this treatment led to the formation of several layer-thick epidermin (left side) while in an adjacent area the epidermis is still very thin (right side). Overall, this combination was somewhat less effective than the AT/PALP/aTF and AT/PALP/aTF/AGP combinations in restoring epidermis in the burnt human skin.

The invention claimed is:

1. A method for stimulating proliferation and promoting survival of cells in the epidermis and dermis of wounded or non-wounded mammalian skin, comprising the step of topically administering to skin a composition comprising therapeutically effective amounts of at least two active proteins, selected from $\alpha_1$-antitrypsin, alkaline phosphatase, transferrin, or $\alpha_1$-acidic glycoprotein.

2. The method of claim 1, wherein the composition comprises alkaline phosphatase and transferrin.

3. The method of claim 2, wherein the composition further comprises $\alpha_1$-antitrypsin.

4. The method of claim 2, wherein the composition further comprises $\alpha_1$-acidic glycoprotein.

5. The method of claim 1, wherein the composition comprises $\alpha_1$-antitrypsin and alkaline phosphatase.

6. The method of claim 5, wherein the composition further comprises $\alpha_1$-acidic glycoprotein.

7. The method of claim 1, wherein the composition comprises $\alpha_1$-antitrypsin and transferrin.

8. The method of claim 7, wherein the composition further comprises $\alpha_1$-acidic glycoprotein.

9. The method of claim 1, wherein the composition further comprises one or more additives or enhancers.

10. The method of claim 1, wherein the composition comprises about 0.05 to about 0.5 wt.-% of each protein with a maximum total protein content of 1 wt.-%.

11. The method of claim 1, wherein the skin is transplanted skin and the composition is administered to an area of the transplanted skin.

12. The method of claim 11, wherein the transplanted skin is human skin.

13. The method of claim 12, wherein the transplanted skin has been transplanted onto a human host.

14. The method of claim 1, wherein the composition is a cream, a lotion, a gel, an unguent, an emollient, a colloidal dispersion, a suspension, an emulsion, an oil, a spray, a foam, or a mousse.

15. The method of claim 1, wherein the composition further comprises a physiologically compatible carrier.

16. The method of claim 15, wherein the carrier comprises *Vaselinum cholesterinatum*.

17. The method of claim 15, wherein the carrier comprises *Vaselinum flavum* or *Vaselinum album*.

18. The method of claim 1, wherein the alkaline phosphatase is placental alkaline phosphatase.

19. The method of claim 1, wherein the human alkaline phosphatase is one of intestinal alkaline phosphatase, non-specific alkaline phosphatase, and germ cell alkaline phosphatase.

20. A regimen for promoting healing of wounds and maintaining or restoring thickness of non-wounded skin by periodic, topical administration to the skin a composition comprising at least two active proteins selected from $\alpha_1$-antitrypsin, alkaline phosphatase, transferrin, or $\alpha_1$-acidic glycoprotein.

21. The regimen of claim 20, wherein the periodic administration includes applying the chosen composition about once a week.

22. A method for stimulating proliferation and promoting survival of cells in the epidermis and dermis of wounded or non-wounded mammalian skin, comprising the step of administering a composition comprising:
a physiologically acceptable carrier; and
therapeutically effective amounts of at least two active protein components selected from $\alpha_1$-antitrypsin, alkaline phosphatase, transferrin, or $\alpha_1$-acidic glycoprotein.

23. A method of claim 20, wherein the injection is intravenous, subcutaneous, intramuscular, intradermal, or intraperitoneal.

24. A method of claim 20, wherein the composition is injected into a mammal, and wherein the therapeutically effective amount of total protein is about 0.01 gram to about 5.0 gram per square meter of calculated surface area for the mammal.

25. A method of claim 22, wherein the carrier is a physiological saline solution.

26. A method of claim 20, wherein the composition is injected into mammalian skin intradermally, and wherein the therapeutically effective amount of total protein is about 0.01 mg to about 1 mg per injection site.

27. The method of claim 20, further comprising the step of administering topically a second composition comprising a physiologically acceptable carrier and at least two active proteins, selected from human $\alpha_1$-antitrypsin, alkaline phosphatase, human transferrin, and $\alpha_1$-acidic glycoprotein.

28. The method of claim 27 wherein the step of administering the second composition is performed simultaneously with the step of injecting the composition.

29. The method of claim 27 wherein the step of administering the second composition is performed consecutively with the step of injecting the composition.

30. The method of claim 27 wherein the second composition comprises the same active protein components as the composition.

31. The method of claim 22 wherein the alkaline phosphatase is placental alkaline phosphatase.

32. A method for stimulating proliferation and promoting survival of transplanted skin cells comprising:
adding at least two active proteins, selected from human $\alpha_1$-antitrypsin, alkaline phosphatase, human transferrin, and human $\alpha_1$-acidic glycoprotein, to a suspension of transplanted skin cell, and
treating the transplanted skin cells following their incorporation and stabilization in host skin.

33. The method of claim 32 wherein the alkaline phosphatase is placental alkaline phosphatase.

34. The method of claim 22, wherein the composition is administered topically.

35. The method of claim 22, wherein the composition is administered by injecting into the skin the composition in a physiologically acceptable carrier.

36. The method of claim 31, further comprising a protease digestion product of human placental alkaline phosphatase.

37. The method of claim 36, wherein the protease is bromelain.

38. The method of claim 22 further comprising a protease digestion product of $\alpha_1$-acidic glycoprotein.

39. The method of claim 22, wherein the transferrin is iron-free human APO-transferrin or iron-containing human holo-transferrin.

* * * * *